US006838437B2

(12) United States Patent
Kaufman et al.

(10) Patent No.: US 6,838,437 B2
(45) Date of Patent: Jan. 4, 2005

(54) INACTIVATION RESISTANT FACTOR VIII

(75) Inventors: Randal J. Kaufman, Ann Arbor, MI (US); Steven W. Pipe, Ypsilanti, MI (US); Kagehiro Amano, Tokyo (JP)

(73) Assignee: University of Michigan, Ann Arbor, MI (US)

(*) Notice: Subject to any disclaimer, the term of this patent is extended or adjusted under 35 U.S.C. 154(b) by 388 days.

(21) Appl. No.: 09/819,098

(22) Filed: Apr. 11, 2001

(65) Prior Publication Data

US 2002/0132306 A1 Sep. 19, 2002

Related U.S. Application Data

(63) Continuation of application No. PCT/US97/06563, filed on Apr. 24, 1997.

(60) Provisional application No. 60/017,785, filed on May 15, 1996, and provisional application No. 60/016,117, filed on Apr. 24, 1996.

(51) Int. Cl.[7] ................................................ A61K 38/00

(52) U.S. Cl. ...................... 514/12; 435/240.2; 424/93.2

(58) Field of Search ........................ 514/12; 435/240.2; 424/93.2

(56) References Cited

U.S. PATENT DOCUMENTS

| | | | | |
|---|---|---|---|---|
| 4,757,006 A | | 7/1988 | Toole, Jr. et al. | 435/68 |
| 4,868,112 A | | 9/1989 | Toole, Jr. | 435/68 |
| 5,004,803 A | | 4/1991 | Kaufman et al. | 530/383 |
| 5,045,455 A | | 9/1991 | Kuo et al. | 435/69.6 |
| 5,214,033 A | | 5/1993 | Zimmerman et al. | 517/21 |
| 5,250,421 A | | 10/1993 | Kaufman et al. | 435/69.6 |
| 5,451,521 A | * | 9/1995 | Kaufman et al. | 435/240.2 |
| 5,563,045 A | | 10/1996 | Pittman et al. | 435/69.6 |
| 5,661,008 A | | 8/1997 | Almstedt et al. | 435/69.6 |

FOREIGN PATENT DOCUMENTS

| | | |
|---|---|---|
| EP | 295597 | 12/1988 |
| EP | 197901 | 7/1991 |
| WO | WO 87/04187 | 7/1987 |
| WO | WO 87/06101 | 10/1987 |
| WO | WO 87/07144 | 12/1987 |
| WO | WO 88/03558 | 5/1988 |
| WO | WO 88/08035 | 10/1988 |
| WO | WO 91/07490 | 5/1991 |
| WO | WO 97/03194 | 1/1997 |
| WO | WO 97/03195 | 1/1997 |
| WO | WO 97/40145 A1 | 10/1997 |

OTHER PUBLICATIONS

Marquette, K, Pittman, D, and Kaufman, R. "A 110–amino acid region within the A1–domain of Coagulation Factor VIII inhibits secretion from mammalian cells." vol. 270, No. 17, pp. 10297–10303, Apr. 28, 1995.*

(List continued on next page.)

*Primary Examiner*—Karen Cochrane Carlson
*Assistant Examiner*—Anand Desai
(74) *Attorney, Agent, or Firm*—Lahive & Cockfield, LLP; DeAnn F. Smith, Esq.

(57) ABSTRACT

The present invention provides novel purified and isolated nucleic acid sequences encoding procoagulant-active FVIII proteins. The nucleic acid sequences of the present invention encode amino acid sequences corresponding to known human FVIII sequences, wherein residue Phe3O9 is mutated. The nucleic acid sequences of the present invention also encode amino acid sequences corresponding to known human FVIII sequences, wherein the APC cleavage sites, Arg336 and Ile562, are mutated. The nucleic acid sequences of the present invention further encode amino acid sequences corresponding to known human FVIII sequences, wherein the B-domain is deleted, the von Willebrand factor binding site is deleted, a thrombin cleavage site is mutated and an amino acid sequence spacer is inserted between the A2- and A3-domains. Methods of producing the FVIII proteins of the invention, nucleotide sequences encoding such proteins, pharmaceutical compositions containing the nucleotide sequences or proteins, as well as methods of treating patients suffering from hemophilia, are also provided.

6 Claims, 16 Drawing Sheets

OTHER PUBLICATIONS

Pittman, D and Kaufman, R. "Proteolytic requirements for thrombin activation of anti–hemophilic factor (factor VIII)." vol. 85, pp. 2429–2433, Apr. 1988.*

Bertina et al. "Mutation in blood coagulation factor V associated with resistance to activated protein C." *Nature.* May 5, 1994;369(6475):64–7.

Blond–Elguindi et al. "Affinity panning of a library of peptides displayed on bacteriophages reveals the binding specificity of BiP." *Cell.* Nov. 19, 1993;75(4):717–28.

Brinkhous et al. "Purified human factor VIII procoagulant protein: comparative hemostatic response after infusions into hemophilic and von Willebrand disease dogs." *PNAS USA*. Dec. 1985;82(24):8752–6.

Castaman et al. "Effectiveness of high–dose intravenous immunoglobulin in a case of acquired von Willebrand syndrome with chronic melena not responsive to desmopressin and factor VIII concentrate." *Am. J. Hematol.* Oct. 1992;41(2):132–6.

Cripe et al. "Structure of the gene for human coagulation factor V." *Biochemistry.* Apr. 21, 1992;31(15):3777–85.

Dahlbäck et al. "Familial thrombophilia due to previously unrecognized mechanism characterized by poor anticoagulant response to activated protein C: prediction of a cofactor to activated protein C." *PNAS USA* Feb. 1, 1993;90(3):1004–8.

Dahlbäck et al. "Inherited resistance to activated protein C is corrected by anticoagulant cofactor activity found to be a property of factor V." *PNAS USA* Feb. 15, 1994;91(4):1396–400.

Davis et al. "The coagulation cascade: initiation, maintenance, and regulation." *Biochemistry.* Oct. 29, 1991;30(43):10363–70.

Dorner et al. "The relationship of N–linked glycosylation and heavy chain–binding protein association with the secretion of glycoproteins." *J. Cell Biol.* Dec. 1987;105(6 Pt 1):2665–74.

Dorner et al. "Increased synthesis of secreted proteins induces expression of glucose–regulated proteins in butyrate–treated Chinese hamster ovary cells." *J. Biol. Chem.* 1989;264(34):20602–7.

Dorner et al. "Protein dissociation from GRP78 and secretion are blocked by depletion of cellular ATP levels." *PNAS USA* Oct. 1990;87(19):7429–32.

Dorner et al. "Overexpression of GRP78 mitigates stress induction of glucose regulated proteins and blocks secretion of selective proteins in Chinese hamster ovary cells." *EMBO J.* Apr. 1992,11(4):1563–71.

Eaton et al. "Proteolytic processing of human factor VIII. Correlation of specific cleavages by thrombin, factor Xa, and activated protein C with activation and inactivation of factor VIII coagulant activity." *Biochemistry.* Jan. 28, 1986;25(2):505–12.

Fay et al. "von Willebrand factor mediates protection of factor VIII from activated protein C–catalyzed inactivation." *J. Biol. Chem.* Feb. 5, 1991;266(4):2172–7.

Fay et al. "Human factor VIIIa subunit structure. Reconstruction of factor VIIIa from the isolated A1/A3–C1–C2 dimer and A2 subunit." *J. Biol. Chem.* May 15, 1991;266(14):8957–62.

Fay et al. "Activated protein C–catalyzed inactivation of human factor VIII and factor VIIIa. Identification of cleavage sites and correlation of proteolysis with cofactor activity." *J. Biol. Chem.* Oct. 25, 1991;266(30):20139–45.

Fay et al. "Role of COOH–terminal acidic region of A1 subunit and in A2 subunit retention in human factor VIIIa." *J. Biol. Chem.* Aug. 25, 1993;268(24):17861–6.

Fay et al. "Factor VIIIa A2 subunit residues 558–585 represent a factor IXa interactive site." *J. Biol. Chem.* Aug. 12, 1994;269(32):20522–7.

Flynn et al. "Peptide binding and release by proteins implicated as catalysts of protein assembly." *Science* Jul. 28, 1989;245(4916):385–90.

Fulcher et al. "Proteolytic inactivation of human factor VIII procoagulant protein by activated human protein C and its analogy with factor V." *Blood* Feb. 1984;63(2):486–9.

Gitschler et al. "Characterization of the human factor VIII gene." *Nature* Nov. 22–28, 1984:312(5992):326–30.

Guinto et al. "The complete cDNA sequence of bovine coagulation factor V." *J. Biol. Chem.* Feb. 15, 1992;267(5):2971–8.

Healey et al. "Residues Glu2181–Val2243 Contain a Major Determinant of the Inhibitory Epitope in the C2 Domain of Human Factor VIII," *Blood,* 1998, 92(10):3701–9.

Jenny et al. "Complete cDNA and derived amino acid sequence of human factor V." *PNAS USA* Jul. 1987;84(14):4846–50.

Kane et al. "Cloning of a cDNA coding for human factor V, a blood coagulation factor homologous to factor VIII and ceruloplasmin." *PNAS USA* Sep. 1986;83(16):6800–4.

Kaufman et al. "Amplification and expression of sequences cotransfected with a modular dihydrofolate reductase complementary DNA gene." *J. Mol. Biol.* Aug. 25, 1982;159(4):601–21.

Kaufman et al. "Identification of the components necessary for adenovirus translational control and their utilization in cDNA expression vectors." *PNAS USA* Feb. 1985;82(3):689–93.

Kaufman et al. "Synthesis, processing, and secretion of recombinant human factor VIII expressed in mammalian cells." *J. Biol. Chem.* May 5, 1988;263(13):6352–62.

Kozutsumi et al. "The presence of malfolded proteins in the endoplasmic reticulum signals the induction of glucose–regulated proteins." *Nature* Mar. 31, 1988;332(6163):462–4.

Koedam et al. "Inactivation of human factor VIII by activated protein C. Cofactor activity of protein S and protective effect on von Willebrand factor." *J. Clin. Invest.* Oct. 1988;82(4):1236–43.

Lenting et al. "Identification of a binding site for blood coagulation factor IXa on the light chain of human factor VIII." *J. Biol. Chem.* Mar. 11, 1994;269(10):7150–5.

Leyte et al. "Sulfation of Tyr1680 of human blood coagulation factor VIII is essential for the interaction of factor VIII with von Willebrand factor." *J. Biol. Chem.* Jan. 15, 1991;266(2):740–6.

Lollar et al. "Structural basis for the decreased procoagulant activity of human factor VIII compared to the porcine homolog." *J. Biol. Chem.* Jul. 5, 1991;266(19):12481–6.

Lusky et al. "Characterization of the bovine papilloma virus plasmid maintenance sequences." *Cell.* Feb. 1984;36(2):391–401.

Mann et al. "Cofactor proteins in the assembly and expression of blood clotting enzyme complexes." *Annu. Rev. Biochem.* 1988;57:915–56.

Marquette et al. "A 110–amino acid region within the A1–domain of coagulation factor VIII inhibits secretion from mammalian cells." *J. Biol. Chem.* Apr. 28, 1995;270(17):10297–303.
Michnick et al. "Identification of individual tyrosine sulfation sites within factor VIII required for optimal activity and efficient thrombin cleavage." *J. Biol. Chem.* Aug. 5, 1994;269(31):20095–102.
Munro et al. "An Hsp70–like protein in the ER: identity with the 78 kd glucose–regulated protein and immunoglobulin heavy chain binding protein." *Cell.* Jul. 18, 1986;46(2):291–300.
Nesheim et al. "The effect of plasma von Willebrand factor on the binding of human factor VIII to thrombin–activated human platelets." *J. Biol. Chem.* Sep. 25, 1991;266(27):17815–20.
Ortel et al. "Structural model of human ceruloplasmin based on internal triplication, hydrophilic/hydrophobic character, and secondary structure of domains." *PNAS USA* Aug. 1984;81(15):4761–5.
Pipe et al., "Construction and characterization of inactivation resistant factor VIII," *Blood,* 88(10):441 (1996).
Pipe et al., "Characterization of a genetically engineered inactivation–resistant coagulation factor Villa." *PNAS USA.* Oct. 28, 1997;94(22):11851–6.
Pittman et al., "Proteolytic requirements for thrombin activation of anti–hemophilic factor (factor VIII)." *Proc. Nat. Acad. Sc.* 85:2429–33 (1988).
Pittman et al. "A2 domain of human recombinant–derived factor VIII is required for procoagulant activity but not for thrombin cleavage." *Blood.* Jan. 15, 1992;79(2):389–97.
Pittman et al. "Post–translational requirements for functional factor V and factor VIII secretion in mammalian cells." *J. Biol. Chem.* Jun. 24, 1994;269(25):17329–37.
Pittman et al. "Role of the B domain for factor VIII and factor V expression and function." *Blood.* Dec. 15, 1994;84(12):4214–25.
Saenko et al. "A novel mechanism for inhibition of factor VIII activity by an antibody with a C2 domain epitope, residues 2248–2285." *Blood* 1995;86 Abstr. 749.
Scandella et al. "Some factor VIII inhibitor antibodies recognize a common epitope corresponding to C2 domain amino acids 2248 thorough 2312, which overlap a phospholipid–binding site." *Blood.* Sep. 1, 1995;86(5):1811–9.
Shima et al. "Common inhibitory effects of human anti–C2 domain inhibitor alloantibodies on factor VIII binding to von Willebrand factor." *Blood.* 1995;86 Abstr. 748.
Shima et al. "Common inhibitory effects of human anti–C2 domain inhibitor alloantibodies on factor VIII binding to von Willebrand factor." *Br. J. Haematol.* Nov. 1995;91(3):714–21.
Stubbs et al. "cDNA cloning of a mouse mammary epithelial cell surface protein reveals the existence of epidermal growth factor–like domains linked to factor VIII–like sequences." *PNAS USA* Nov. 1990;87(21):8417–21.
Sun et al. "Blood coagulation factor Va abnormality associated with resistance to activated protein C in venous thrombophilia." *Blood.* Jun. 1, 1994;83(11):3120–5.
Svensson et al. "Resistance to activated protein C as a basis for venous thrombosis." *N. Engl. J. Med.* Feb. 24, 1994;330(8):517–22.
Swaroop, M. et al., "Mutation of Phe309Ser, a putative BIP binding site, enhances secretion of coagulation factor VIII," *Blood,* 88(10):441a (1996).
Takahashi et al, "Single–chain structure of human ceruloplasmin: the complete amino acid sequence of the whole molecule." *PNAS USA.* Jan. 1984; 81(2):390–4.
Toole et al. "Molecular cloning of a cDNA encoding human antihaemophilic factor." *Nature.* Nov. 22–28, 1984;312(5992):342–7.
Toole et al. "A large region (approximately equal to 95 kDa) of human factor VIII is dispensable for in vitro procoagulant activity." *PNAS USA* Aug. 1986;83(16):5939–42.
Toole, J. J. et al., "Exploration of structure–function relationships in human factor VIII by site–directed mutagenesis." *Cold Spring Harbor Symposia on Quantitative Biology,* 51(1):543–9 (1986).
Varadi et al. "Influence of factor V and factor Va on APC–induced cleavage of human factor VIII." *Thromb. Haemost.* Apr. 1995;73(4):730–1.
Varadi et al. "A chromogenic assay for activated protein C resistance." *Br. J. Haematol.* Aug. 1995;90(4):884–91.
Vehar et al. "Structure of human factor VIII." *Nature.* Nov. 22–28, 1984;312(5992):337–42.
Walker et al. "Inactivation of factor VIII by activated protein C and protein S." *Arch. Biochem. Biophys.* Jan. 1987;252(1):322–8.
Walker et al. "Identification of the binding site for activated protein C on the light chain of factors V and VIII." *J. Biol. Chem.* Jan. 25, 1990;265(3):1484–9.
Wood et al. "Expression of active human factor VIII from recombinant DNA clones." *Nature.* Nov. 22–28, 1984;312(5992):330–7.

* cited by examiner

Figure 2

Activity in conditioned medium from transiently transfected COS-1 cells (compared to wild-type).

| Residue | FVIII Sequence<br>ITFLTAQTLLMDLGQFL LFCHISS<br>291 … 314 | FVIII Activity |
|---|---|---|
| 7(F,L-A) | AA A AA AA | Not Detected |
| F293S | S | No Effect |
| F306W | W | No Effect |
| F306/309W,S | W S | 1.6x ↑ |
| L,F308/309E,S | ES | 1.9x ↑ |
| Q,F305/309K,S | K S | 2.0x ↑ |
| F309S | S | 1.9x ↑ |

INACTIVATION RESISTANT FACTOR VIII

RELATED APPLICATIONS

The present application is a continuation and claims priority under 35 U.S.C. §120 from PCT International Application No. PCT/US97/06563, filed Apr. 24, 1997, which is a continuation-in-part of U.S. Ser. No. 60/016,117, filed Apr. 24, 1996 and U.S. Ser. No. 60/017,785, filed May 15, 1996, all hereby expressly incorporated by reference.

SPONSORSHIP

Work on this invention was supported by the United States Government under grants HL53777 and HL52173 awarded by the National Institutes of Health. The government may have certain rights in this invention.

FIELD OF THE INVENTION

The present invention relates generally to procoagulant-active proteins and more particularly, nucleotide sequences encoding factor VIII protein capable of secretion at levels higher than typically obtained with wild-type factor VIII, APC resistant factor VIII protein and inactivation resistant factor VIII protein.

BACKGROUND OF THE INVENTION

Human factor VIII:C (FVIII) is the coagulation factor deficient in the X-chromosome-linked bleeding disorder hemophilia A, a major source of hemorrhagic morbidity and mortality in affected males. Traditionally, hemophiliacs were treated with transfusions of whole blood. More recently, treatment has been with preparations of FVIII concentrates derived from human plasma. However, the use of plasma-derived product exposes hemophiliac patients to the possible risk of virus-transmissible diseases such as hepatitis and AIDS. Costly purification schemes to reduce this risk increases treatment costs. With increases in costs and limited availability of plasma-derived FVIII, patients are treated episodically on a demand basis rather than prophylactically. Recombinantly produced FVIII has substantial advantages over plasma-derived FVIII in terms of purity and safety, as well as increased availability and accordingly, much research effort has been directed towards the development of recombinantly produced FVIII. Due to the labile nature of FVIII, especially following its activation, large and repeated doses of protein whether plasma or recombinantly-derived, must be administered to achieve a therapeutic benefit. However, the amount of FVIII protein the patient is exposed to has been correlated with the development of antibodies which inhibit its activity. In light of this known immunogenicity, one of the goals in developing new recombinant forms of FVIII for use as a therapeutic agent is the development of products that reduce or eliminate such an immune response.

FVIII functions in the intrinsic pathway of blood coagulation as a cofactor to accelerate the activation of factor X by factor IXa, a reaction that occurs on a negatively charged phospholipid surface in the presence of calcium ions. FVIII is synthesized as a 2351 amino acid single-chain polypeptide having the domain structure A1-A2-B-A3-C1-C2. Wehar, G. A. et al., *Nature* 312:337–342 (1984) and Toole, J. J. et al., *Nature* 312:342–347 (1984). The domain structure of FVIII is identical to that of the homologous coagulation factor, factor V (FV). Kane, W. H. et al., *PNAS* (*USA*) 83:6800–6804 (1986) and Jenny, R. J. et al., *PNAS* (*USA*) 84:4846–4850 (1987). The FVIII A-domains are 330 amino acids and have 40% amino acid identity with each other and to the A-domain of FV and the plasma copper-binding protein ceruloplasmin. Takahashi, N. et al., *PNAS* (*USA*) 81:390–394 (1984). Each C-domain is 150 amino acids and exhibits 40% identity to the C-domains of FV, and to proteins that bind glycoconjugates and negatively charged phospholipids. Stubbs, J. D. et al., *PNAS* (*USA*) 87:8417–8421 (1990). The FVIII B-domain is encoded by a single exon and exhibits little homology to any known protein including FV B-domain. Gitschier, J. et al., *Nature* 312:326–330 (1984) and Cripe, L. D. et al., *Biochemistry* 31:3777–3785 (1992).

FVIII is secreted into plasma as a heterodimer of a heavy chain (domains A1-A2-B) and a light chain (domains A3-C1-C2) associated through a noncovalent divalent metal ion linkage between the A1- and A3-domains. In plasma, FVIII is stabilized by binding to von Willebrand factor. More specifically, the FVIII light chain is bound by noncovalent interactions to a primary binding site in the amino terminus of von Willebrand factor. Upon proteolytic activation by thrombin, FVIII is activated to a heterotrimer of 2 heavy chain fragments (A1, a 50 kDa fragment, and A2, a 43 kDa fragment) and the light chain (A3-C1-C2, a 73 kDa chain). The active form of FVIII (FVIIIa) thus consists of an A1-subunit associated through the divalent metal ion linkage to a thrombin-cleaved A3-C1-C2 light chain and a free A2 subunit associated with the A1 domain through an ion association (see FIG. 1A). Eaton, D. et al., *Biochemistry* 25: 505 (1986); Lollar, P. et al., *J. Biol. Chem.* 266: 12481 (1991); and Fay, P. J. et al., *J. Biol. Chem.* 266: 8957 (1991). This FVIIIa heterotrimer is unstable and subject to rapid inactivation through dissociation of the A2 subunit under physiological conditions.

Previous transfection studies demonstrated that FVIII is 10-fold less efficiently secreted than FV. The inefficient secretion of FVIII correlates with binding to the protein chaperonin identified as the immunoglobulin binding protein (BiP), also known as the glucose-regulated protein of 78 kDa (GRP78) (Munro, S. et al., *Cell* 46:291–300 (1986)) within the lumen of the ER (Dorner, A. J. et al., *EMBO J.* 4:1563–1571 (1992)). BiP is a member of the heat-shock protein family that exhibits a peptide-dependent ATPase activity. Flynn, G. C. et al., *Science* 245:385–390 (1989). BiP expression is induced by the presence of unfolded protein or unassembled protein subunits within the ER. Lee, A. S., *Curr. Opin. Cell Biol.* 4:267–273 (1992) and Kozutsumi, Y. et al., *Nature* 332:462464 (1988). It has been shown that high level FVIII expression induces BiP transcription. Dorner, A. J. et al., *J. Biol. Chem.* 264:20602–20607 (1989). In addition, FVIII release from BiP and transport out of the ER requires high levels of intracellular ATP. Dorner, A. J. et al., *PNAS* (*USA*) 87:7429–7432 (1990). In contrast, it has been found that FV does not associate with BiP and does not require high levels of ATP for secretion. Pittman, D. D. et al., *J. Biol. Chem.* 269: 17329–17337 (1994). Deletion of the FVIII-B-domain yielded a protein that bound BiP to a lesser degree and was more efficiently secreted. Dorner, A. J. et al., *J. Cell Biol.* 105:2665–2674 (1987). To evaluate whether the FVIII B-domain was responsible for BiP interaction, FV and FVIII chimeric cDNA molecules were constructed in which the B-domain sequences were exchanged. Pittman, D. D. et al., *Blood* 84:42144225 (1994). A FVIII hybrid harboring the B-domain of FV was expressed and secreted as a functional molecule, although the secretion efficiency of the hybrid was poor, similar to wild-type FVIII. Pittman, D. D. et al., *Blood* 84:42144225 (1994). This indicated that the difference in secretion efficiency between FV and FVIII was not directly attributable to specific sequences within the FVIII B-domain, the most divergent region between these homologous coagulation factors.

To determine whether specific amino acid sequences within FVIII A-domain inhibit secretion, chimeric proteins containing the A1- and A2-domains of FVIII or FV were studied. The chimeric protein containing the A1- and A2-domains of FV was secreted with a similar efficiency as wild-type FV. The complementary chimera having the A1- and A2-domains of FVIII was secreted with low efficiency similar to wild-type FVIII. These results suggested that sequences within the A1- and A2-domains were responsible for the low secretion efficiency of FVIII. An A1-domain-deleted FVIII molecule was constructed and secretion was increased approximately 10-fold compared to wild-type FVIII A2-domain-deleted FVIII. Expression of the FVIII A1-domain alone did not yield secreted protein, whereas expression of the FVIII A2-domain alone or the FV A1-domain or A2-domain alone directed synthesis of secreted protein. Secretion of a hybrid in which the carboxyl-terminal 110 amino acids of the A1-domain were replaced by homologous sequences from the FV A1-domain (226–336 hybrid FVIII) was also increased 10-fold compared to wild-type FVIII, however, the secreted protein was not functional, i.e. did not display procoagulant activity, and the heavy and light chains were not associated. Marquette, K. A. et al., *J. Biol. Chem.* 270:10297–10303 (1995). It would thus be desirable to provide a functional recombinant FVIII protein having increased secretion as compared to wild-type FVIII. It would also be desirable to provide a functional recombinant FVIII protein with increased secretion as well as increased specific activity.

FVa and FVIIIa are inactivated by Activated protein C (APC) in the presence of phospholipid and $CaCl_2$ and APC-resistance has been considered to be one of the major causes of hereditary thrombophilia. Dahlbäck, B. et al., *PNAS* (*USA*) 90: 1004 (1993). The molecular basis for the APC-resistance was attributed to resistance to APC cleavage and inactivation. Dahlbäck, B. et al., *PNAS* (*USA*) 91: 1396 (1994). Previous studies on the APC inactivation of FVIII noted the generation of a 45 kDa fragment (Fulcher, C. A. et al., *Blood* 63: 486 (1984)) derived from the amino-terminus of the heavy chain and was proposed to result from cleavage at Arg336. Eaton, D. et al., *Biochemistry* 25: 505 (1986). While the light chain of FVIII is not cleaved by APC, multiple polypeptides, representing intermediate and terminal digest fragments derived from the heavy chain, have been observed. Walker, F. J. et al., *Arch. Bioch. Biophys.* 252: 322 (1987). These fragments result from cleavage site locations at Arg336, the junction of the A1 and A2 domain, at Arg562, bisecting the A2 domain, and a site at the A2-B junction, likely at Arg740. Fay, P. J. et al., *J. Biol. Chem.* 266: 20139 (1991). APC cleavage of FVIII at residue 336 generates a 45 kDa fragment from the amino-terminus of the A1-domain and cleavage at residues 562 and 740 generates a 25 kDa, fragment from the carboxy-terminus of the A2-domain (see FIG. 1A).

Previous studies have demonstrated that the B-domain of FVIII is dispensable for FVIII cofactor activity. Genetically engineered FVIII molecules that have varying degrees of B-domain deletion (BDD) yield secreted single chain FVIII species in which no intracellular proteolysis of the primary translation product is observed. These BDD FVIII mutants are advantageous because they are more efficiently produced in mammalian cells. Functional characterization of these BDD FVIII molecules demonstrated that FVIII cofactor activity is retained if thrombin cleavage after Arg372, Arg740 and Arg1689 occurs. Therefore, any functional construction of FVIII genetically engineered thus far generates a FVIIIa heterotrimer following thrombin activation. The functional advantages of previous BDD FVIII constructs has therefore been limited by rapid dissociation of the non-covalently linked A2 subunit from FVIIIa.

It would thus be desirable to provide improved recombinant FVIII protein. It would also be desirable to provide FVIIIa protein that is resistant to activation. It would further be desirable to provide FVIIIa protein that is APC-resistant. It would also be desirable to provide FVIII protein having increased secretion as compared to wild-type FVIII. It would further be desirable to provide FVIII protein having increased secretion and APC-resistance. It would also be desirable to provide FVIII protein having increased secretion and inactivation resistance. It would also be desirable to provide a method of treating hemophiliac patients with improved recombinant FVIII. It would further be desirable to provide a method for treating hemophiliac patients via replacement therapy, wherein the amount of FVIII protein required to treat the patient is decreased.

SUMMARY OF INVENTION

The present invention provides novel purified and isolated nucleic acid sequences encoding procoagulant-active FVIII protein. In one embodiment, the nucleic acid sequences of the present invention encode amino acid sequences corresponding to known human FVIII sequences, wherein the A1-domain, specifically amino acid residue 309, phenylalanine, is mutated. In a preferred embodiment, Phe309 is either deleted or substituted with any other amino acid residue, preferably serine. The resulting FVIII protein is capable of secretion at levels higher than typically obtained with wild-type FVIII and retains procoagulant activity.

In another embodiment, the nucleic acid sequences of the present invention encode amino acid sequences corresponding to known human FVIII sequences wherein APC cleavage sites have been mutated. In a preferred embodiment, amino acid residues 336 and 562 are mutated preferably from arginine to isoleucine and arginine to lysine, respectively. The resulting FVIII protein is APC resistant and thus for convenience, is generally referred to herein as “APC resistant FVIII.”

In yet another embodiment, the nucleic acid sequences of the present invention encode amino acid sequences corresponding to known human FVIII sequences wherein the B-domain is deleted, the von Willebrand factor binding site is deleted, a thrombin cleavage site is mutated, and an amino acid sequence spacer is inserted between the A2- and A3-domains. In a preferred embodiment, the thrombin cleavage site Arg740 is mutated, preferably by substitution with alanine. In another preferred embodiment, the amino acid sequence spacer is the amino portion of the B-domain, preferably the 54 residues of the amino portion of the B-domain. In yet another preferred embodiment, one or both of the APC cleavage sites is mutated, as described herein. It has been surprisingly found that upon activation by thrombin, this protein is a heterodimer, wherein the A2-domain remains covalently associated with the light chain (see FIG. 1B). This heterodimer configuration is more stable than the wild-type heterotrimer configuration and has an approximate five-fold increase in specific activity compared to purified wild-type FVIII. Thus, in a preferred embodiment, the FVIII of the present invention is secreted as a single-chain polypeptide which, upon activation by thrombin, achieves an inactivation resistant FVIII heterodimer. For convenience, this novel FVIII of the present invention is generally referred to herein as "inactivation resistant FVIII."

In a further embodiment, the inactivation resistant FVIII of the present invention may be induced to bind to von Willebrand factor (vWF). It has been found that in the presence of an anti-light chain antibody, ESH8, the inactivation resistant FVIII of the present invention, which lacks the vWF binding site, has an increased binding affinity to vWF. Such an antibody or other cross-linking agent which induces binding to vWF may, therefore, be used to further stabilize the inactivation resistant FVIII of the present invention.

In yet a further embodiment, the nucleic acid sequences of the present invention encode APC resistant FVIII amino acid sequences having a mutation at residue 309, phenylalanine. Preferably, Phe309 is deleted or substituted with another amino acid, e.g., serine. The nucleic acid sequences of the present invention may also encode inactivation resistant FVIII amino acid sequences having a mutation at Phe309. Again, Phe309 is preferably deleted or substituted with another amino acid, e.g., serine. Thus, the nucleic acid sequences of the present invention encode FVIII proteins that exhibit inactivation resistance and/or increased secretion.

It will be appreciated to those skilled in the art that due to the inactivation resistance of the proteins of the present invention and accompanying increased specific activity, a lower dosage of protein may be administered to hemophiliac patients during FVIII replacement therapy. Thus, by utilizing the proteins of the present invention, the total exposure of protein to the patient is reduced, thereby lowering the likelihood of inhibitor formation. It will further be appreciated that the novel FVIII of the present invention will also be useful in gene therapy applications.

Additional objects, advantages, and features of the present invention will become apparent from the following description and appended claims, taken in conjunction with the accompanying drawings.

BRIEF DESCRIPTION OF THE DRAWINGS

The various advantages of the present invention will become apparent to one skilled in the art by reading the following specification and subjoined claims and by referencing the following drawings in which:

FIG. 2 is a table showing secretion activity of the A-1 mutated FVIII proteins of the present invention compared to wild-type FVIII (SEQ ID NO: 3);

DETAILED DESCRIPTION OF THE PREFERRED EMBODIMENTS

Figure 1A:
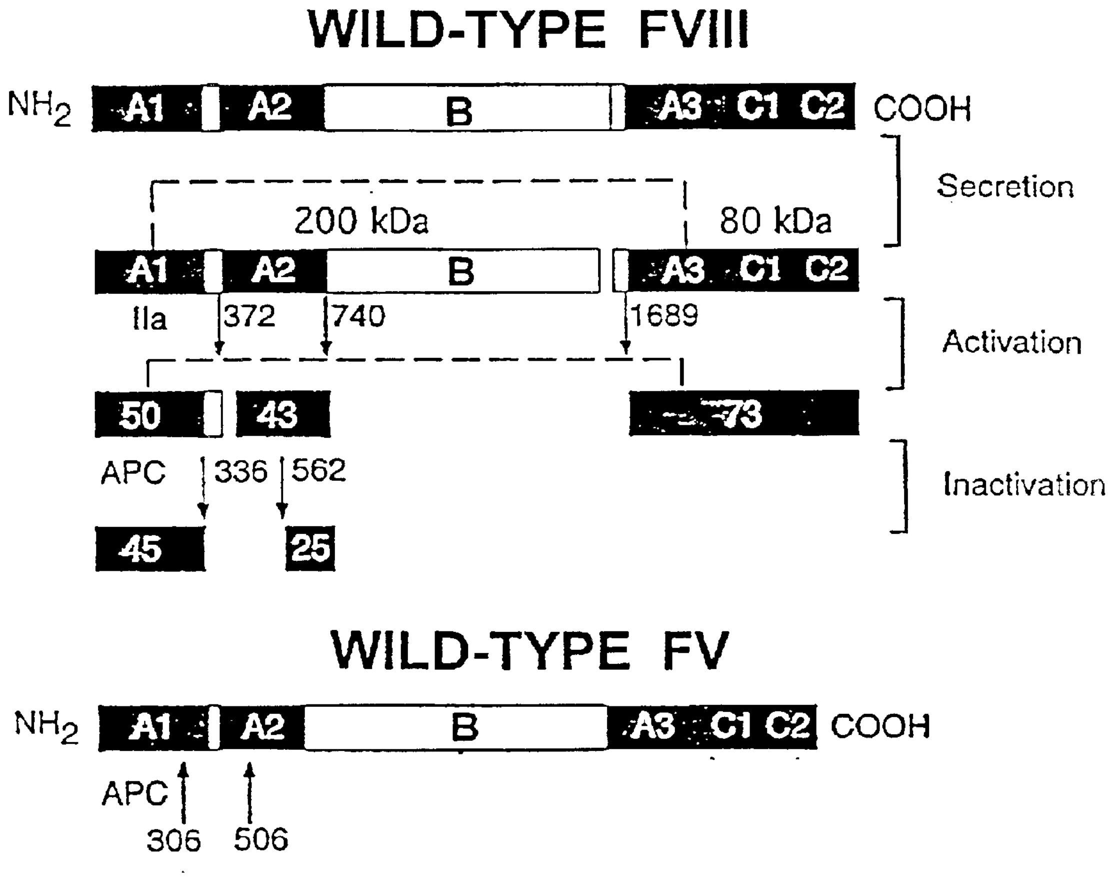
FIG. 1A is a diagram of the wild-type FVIII and FV domain structures.
Figure 1B:
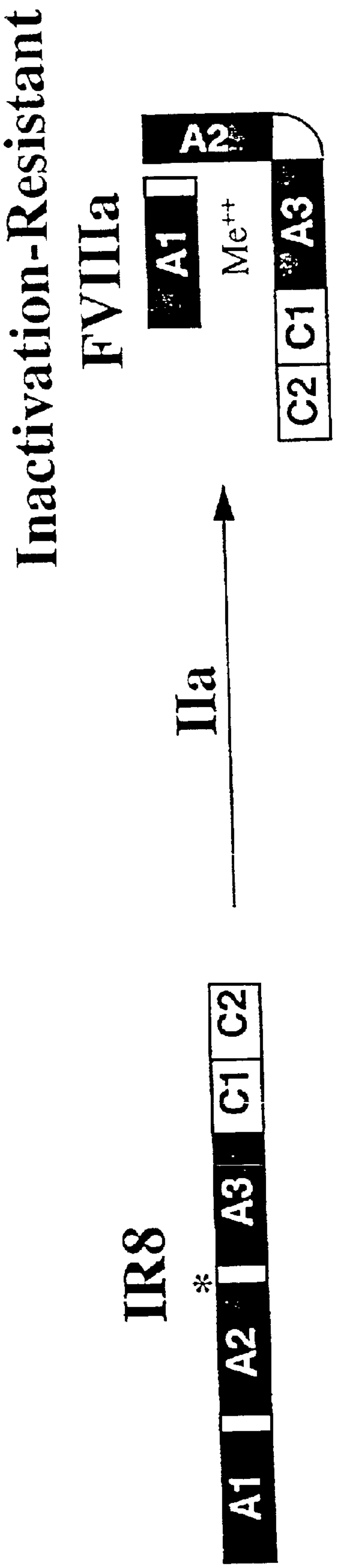
FIG. 1B is a diagram of the inactivation resistant FVIII of the present invention.

Novel purified and isolated nucleic acid sequences encoding procoagulant-active FVIII are provided. Nucleic acid sequences encoding amino acid sequences corresponding to known human FVIII sequences, that include an A1-domain mutation are provided. More specifically, nucleic acid sequences are provided that encode amino acid sequences corresponding to known human FVIII sequences wherein amino acid residue 309, phenylalanine, is mutated. In a preferred embodiment, Phe309 is either deleted or substituted with any other amino acid residue, preferably serine. The resulting FVIII protein is capable of secretion at levels higher than typically obtained with wild-type FVIII and retains procoagulant activity.

Nucleic acid sequences encoding amino acid sequences corresponding to known human FVIII sequences containing mutated APC cleavage sites are also provided. In a preferred embodiment, the APC cleavage sites Arg336 and Arg562 are mutated, preferably to isoleucine and lysine, respectively (R336I and R562K). The resulting FVIII protein is APC resistant.

Nucleic acid sequences are also provided which encode amino acid sequences corresponding to known human FVIII sequences, wherein the B-domain is deleted, the von Willebrand factor binding site (i.e., the acidic region of the amino terminus of the light chain) is deleted, a thrombin cleavage site is mutated, and an amino acid sequence spacer is inserted between the A2- and A3-domains. This embodiment may further include an APC cleavage site mutation, for example one or both of the APC cleavage site mutations described herein. In a preferred embodiment, the thrombin cleavage site Arg740 is mutated, preferably by substitution with alanine (R740A) or lysine (R740K). The amino acid sequence spacer is of a sufficient length to allow the protein to be activated by thrombin to achieve a heterodimer, wherein the A2-domain remains covalently associated with the light chain. In a preferred embodiment, the spacer is approximately 54 residues in length. In another preferred embodiment, the spacer comprises the 54 residues of the amino portion of the wild-type FVIII B-domain, i.e. residues 741 to 794, wherein residue 794 is threonine or leucine. The single-chain polypeptide (novel FVIII, also referred to herein as IR8) upon activation with thrombin, becomes a heterodimer (novel FVIIIa, also referred to herein as IR8a), having an approximate five-fold increase in specific activity compared to purified wild-type FVIII.

In a further embodiment, the inactivation resistant FVIII of the present invention may be employed in combination with an antibody or cross-linking agent which increases the protein's binding affinity to vWF. For example, when the vWF binding site-deleted inactivation resistant FVIII of the present invention is in the presence of ESH8, a commercially available mouse monoclonal antibody (American Diagnostics, Inc. Greenwich, Conn.), which recognizes an epitope at amino acids 2248 to 2285 within the C2-domain, the inactivation resistant FVIII binds to vWF. As set forth in greater detail in Example 4, the inactivation resistant FVIII of the present invention has at least a 10-fold reduced affinity for vWF compared to wild-type FVIII, however, in the presence of ESH8, it has only a 2-fold reduced affinity for vWF. It has recently been reported that ESH8 can function as an inhibitor of wild-type FVIII activation by increasing the affinity of thrombin-cleaved FVIII (FVIIIa) for vWF. Saenko, E. L. et al., *Blood* 86, Abstract No. 749 (1995). By delaying the release of FVIIIa from vWF, A2 dissociation and further proteolytic cleavages likely inactivate the FVIIIa before it can fully release from vWF and exert its cofactor function. A human inhibitor antibody that recognizes an epitope at amino acids 2218 to 2307 within the C2-domain has also been reported that appears to inhibit wild-type FVIII activation by a similar mechanism and may similarly be used to induce vWF binding. Shima, M. et al., *Blood* 86, Abstract No. 748 (1995) and Shima, M. et al., *British J. Hematol.* 91: 714–721 (1995).

In yet a further embodiment, the nucleic acid sequences of the present invention encode APC resistant FVIII described herein, having an additional mutation at Phe309. Preferably, Phe309 is deleted or substituted with another amino acid, e.g., serine. The nucleic acid sequences of the present invention may also encode inactivation resistant FVIII described herein, also having an additional mutation at Phe309. Again, Phe309 is preferably deleted or substituted with another amino acid, e.g., serine. Thus, the nucleic acid sequences of the present invention encode FVIII proteins that exhibit inactivation resistance and/or increased secretion.

It will be appreciated that due to the increased specific activity of the proteins of the present invention, a lower dosage of protein may be administered to hemophiliac patients while maintaining therapeutically effective FVIII activity levels. In addition to cost savings, by utilizing the proteins of the present invention in FVIII replacement therapy, the total exposure of protein to the patient is reduced, thereby lowering the likelihood of inhibitor formation. It will further be appreciated that the proteins of the present invention are also useful in gene therapy-related treatment.

DNA sequences for human FVIII are known, as are expression methods (see, e.g. Toole et al., *Nature* 312:312–317 (1984); Wood et al., *Nature* 312:330–337, Vehar et al., *Nature* 312:337–342, U.S. Pat. No. 4,757,006, WO 87/04187, WO 88/08035 and WO 88/3558). The novel purified and isolated nucleic acid sequences encoding the FVIII protein of the present invention, i.e. a nucleic acid sequence encoding a polypeptide sequence substantially the same as human FVIII or variants thereof modified as is known in the art and described herein, may be made by conventional techniques. For example, the mutations at Phe309 and the APC and thrombin cleavage sites may thus be made by site-directed mutagenesis of the cDNA. One of skill in the art will recognize that "mutation" refers to any alteration including but not limited to, substitutions, insertions and deletions. It will further be appreciated that the remainder of the FVIII nucleic acid sequence may vary from the wild-type FVIII by containing additional modifications such as those disclosed in U.S. Pat. No. 5,004,803, WO 86/06101, and WO 87/07144. FVIII analogs have been developed to better understand the specific structural requirements for FVIII activatibility, inactivatibility, and in vivo efficacy and are also within the scope of the present invention. Included among the features to be optimized are simplified preparation, ease of administration, stability, improved clearance/distribution characteristics, reduced immunogenicity, and prolonged half-life. Moreover, it will be appreciated that variant FVIII nucleic acid sequences in accordance with the present invention also include allelic variations, i.e. variations in sequence due to natural variability from individual to individual, or with other codon substitutions or deletions which still retain FVIII-type procoagulant activity.

Alternate nucleic acid forms, such as genomic DNA, cDNA, and DNA prepared by partial or total chemical synthesis from nucleotides, as well as DNA with mutations, are also within the contemplation of the invention.

Association of nucleic acid sequences provided by the invention with homologous or heterologous species expression control sequences, such as promoters, operators, regulators, and the like, allows for in vivo and in vitro transcription to form mRNA which, in turn, is susceptible to translation to provide novel FVIII proteins and related poly- and oligo-peptides in large quantities. The present invention thus comprises the expression products of the nucleic acid sequences of the invention, as well as activated forms of these expression products. In a presently preferred expression system of the invention, FVIII encoding sequences are operatively associated with a regulatory promoter sequence allowing for transcription and translation in a mammalian cell to provide, for example, FVIII having clotting activity.

As used herein the term "procoagulant-active" and "active" FVIII, may be used interchangeably to refer to one or more polypeptide(s) or proteins demonstrating procoagulant activity in a clotting assay. The term FVIII may be used herein to encompass FVIIIa and one skilled in the art will appreciate from the context in which the terms are used which term (pre-thrombin activated FVIII or thrombin activated FVIII (FVIIIa)) is intended. As used herein, the term "polypeptides" includes not only full length protein molecules but also fragments thereof which, by themselves or with other fragments, generate FVIII procoagulant activity in a clotting assay. It will be appreciated that synthetic polypeptides of the novel protein products of the present invention are also within the scope of the invention and can be manufactured according to standard synthetic methods. It will also be appreciated that in the amino acid numbering system used herein, amino acid residue 1 is the first residue of the native, mature FVIII protein. It will further be appreciated that the term "domain" refers to the approximate regions of FVIII, known to those skilled in the art.

As used herein, the phrase "a sequence substantially corresponding to the sequence" is meant to encompass those sequences which hybridize to a given sequence under stringent conditions as well as those which would hybridize but for the redundancy of the genetic code and which result in expression products having the specified activity. Stringent conditions are generally 0.2×SSC at 65° C. The phrase "substantially duplicative" is meant to include those sequences which, though they may not be identical to a given sequence, still result in expression product, proteins, and/or synthetic polypeptides that have FVIII activity in a standard clotting assay.

The incorporation of the sequences of the present invention into prokaryotic and eucaryotic host cells by standard transformation and transfection processes, potentially involving suitable viral and circular DNA plasmid vectors, is also within the contemplation of the invention. Prokaryotic and eucaryotic cell expression vectors containing and capable of expressing the nucleic acid sequences of the present invention may be synthesized by techniques well known to those skilled in this art. The components of the vectors such as the bacterial replicons, selection genes, enhancers, promoters, and the like, may be obtained from natural sources or synthesized by known procedures (see, e.g. Kaufman et al., *J. Mol. Biol.* 159:601–621 (1982) and Kaufman, *PNAS* 82:689–693 (1995)). Expression vectors useful in producing proteins of this invention may also contain inducible promoters or comprise inducible expression systems as are known in the art.

Established cell lines, including transformed cell lines, are suitable as hosts. Normal diploid cells, cell strains derived from in vitro culture of primary tissue, as well as primary explants (including relatively undifferentiated cells such as hematopoietic stem cells) are also suitable. Candidate cells need not be genotypically deficient in the selection gene so long as the selection gene is dominantly acting.

The use of mammalian host cells provides for such post-translational modifications, e.g. proteolytic processing, glycosylation, tyrosine, serine, orthreonine phosphorylation, as may be made to confer optimal biological activity on the expression products of the invention. Established mammalian cell lines are thus preferred, e.g. CHO (Chinese Hamster Ovary) cells. Alternatively, the vector may include all or part of the bovine papilloma virus genome (Lusky et al., *Cell* 36:391–401 (1984)) and be carried in cell lines such as C127 mouse cells as a stable episomal element. Other usable mammalian cell lines include HeLa, COS-1 monkey cells, melanoma cell lines such as Bowes cells, mouse L-929 cells, 3T3 lines derived from Swiss, Balb-c or NIH mice, BHK or HaK hamster cell lines, and the like.

Whichever type of expression vector is used, it may be preferable to co-express the FVIII nucleic acids of the present invention with a nucleic acid sequence encoding von Willebrand factor (vWF) or an analog thereof, e.g. as described in WO 87/06101, WO 88/08035 and U.S. Pat. No. 5,250,421. It may also be preferred to express the protein in media containing a protease inhibitor such as aprotinin, e.g. in an amount from about 0.01 to about 5%, preferably from about 0.5 to about 1.0%, (vol/vol) (Aprot., 15–30 Trypsin inhibitor units (TIU)/ml, Sigma) or corresponding amounts of activity units of other protease inhibitors.

Stable transformants are screened for expression of the procoagulant product by standard immunological or activity assays. The presence of the DNA encoding the procoagulant proteins may be detected by standard procedures such as Southern blotting. Transient expression of the procoagulant genes during the several days after introduction of the expression vector into suitable host cells such as COS-1 monkey cells, is measured without selection by activity or immunologic assay of the proteins in the culture medium. Following the expression of the DNA by conventional means, the protein so produced may be recovered, purified and/or characterized with respect to physicochemical, biochemical and/or clinical parameters, all by known methods.

In a further embodiment, the nucleotide sequences of the present invention may be used in gene therapy applications, e.g. to treat hemophilia caused by deficiency of FVIII. Due to the increased specific activity of the FVIII proteins of the present invention, therapeutically effective FVIII activity may be achieved with lower protein expression levels as compared to other forms of FVIII including wild-type FVIII. The methods of this invention thus comprise the step of introducing the nucleotide sequences of the present invention into a target cell. In order to effectuate transfer, the nucleotide sequences to be transferred must be associated with a vehicle capable of transducing the target cell. Those skilled in the art will appreciate that such vehicles include known gene therapy delivery systems including, but not limited to, adenoviral, retroviral and adeno-associated viral vectors, as well as liposomes and DNA-protein complexes.

The invention will be further understood with reference to the following illustrative examples and procedures, which is purely exemplary, and should not be taken as limiting the true scope of the present invention. Example 1 describes the preparation and analysis of the A1-domain mutated FVIII of the present invention. Example 2 describes the preparation and analysis of the APC resistant FVIII of the present invention. Example 3 describes the preparation and analysis of the inactivation resistant FVIII of the present invention. Example 4 describes the inducible vWF-binding of the inactivation resistant FVIII of the present invention. Example 5 describes pharmaceutical compositions and methods of use of the FVIII proteins and nucleotide sequences of the present invention.

EXAMPLE 1

Preparation and Analysis of A1-domain Mutated Factor VIII

A statistical algorithm (Blond-Elguindi, S. et al., *Cell* 75:717–728 (1993)) was applied to predict the BiP binding potential of 7-mer peptides to the 226–336 region of FVIII (residue 1 is the first amino acid residue of the native, mature FVIII protein). Residues Leu303 to Phe309 were found to have a BiP binding score of +14 where any score over +10 has an extremely high probability of binding BiP. Fay, P. J. et al., *J. Biol. Chem.* 266:8957–8962 (1991). This region contains a hydrophobic cluster where 7 of 11 amino acid residues are Leu or Phe.

Initially all 7 Leu and Phe residues in the potential BiP binding pocket were mutated to Ala. Site-directed mutagenesis by oligonucleotide overlap-extension polymerase chain reaction (PCR) mutagenesis was utilized. A FVIII/FV chimeric was produced wherein residues 226–336 of FVIII were replaced with the homologous residues from FV (residues 198–313). Marquette, K. A. et al., *J. Biol. Chem.* 270:10297–10303 (1995). Partially complementary primers that contained the mutation were utilized with two primers directed at the MluI sites at 226 and 336 in the FVIII/FV chimeric cDNA to amplify two overlapping products that contain the directed mutation. These two fragments were isolated and fused together by PCR using the two MluI site containing primers. The resultant MluI fragment was then subcloned into the MluI digested FVIII/FV 226–336 chimera within the expression vector pMT2. All mutations were confirmed by DNA sequencing over the PCR amplified region. Expression vectors encoding these mutants were transfected into COS-1 cells and the conditioned medium taken at 60 hr for analysis of FVIII activity by Coatest activity assay. When all 7 Leu and Phe residues in the potential BiP binding pocket were mutated to Ala, the molecule was not secreted. Subsequently, the Phe residues were individually mutated to the respective amino acid residues in FV. The secretion of the F309S mutants (either alone or in combination with other mutants) were reproducibly increased 2-fold in several transfection experiments. As shown in FIG. 2, mutations at other adjacent residues (F293S, F306W) did not improve secretion. The increased secretion of the F309S mutants correlated with a 2-fold increase in FVIII antigen, indicating a specific activity similar to wild-type FVIII. Metabolic labeling with [$^{35}$S]-methionine for 20 min with a 4 hr chase in medium containing excess unlabeled methionine indicated that the increased secretion of the F309 and Q,F305/309K,S mutants correlated with increased secretion compared to wild-type FVIII.

Stably transfected CHO cell lines were engineered that express the F309S mutant. Of 35 original transfected CHO cell clones selected for dihydrofolate reductase expression, 5 clones were obtained that express significant levels of FVIII (approximately 1 U/ml/$10^6$ cells/day). Two of these clones express the same level of FVIII as the original 10A1 cell line that was obtained by screening over 1000 original transfected cell clones. Kaufman, R. J. et al., *J. Biol. Chem.* 263:6352–6362 (1988). Thus, in low concentrations of methotrexate, the mutation permits high level FVIII expression to be obtained more readily.

Further selection in methotrexate is performed to determine if the maximum productivity of FVIII/cell is improved. Experiments are performed to measure BiP interaction and ATP dependence for secretion for the F309W/S functional FVIII mutant in the stably transfected CHO cells.

EXAMPLE 2

Preparation and Analysis of APC Resistant Factor VIII

Experimental Procedures

Materials. FVIII deficient plasma and normal pooled human plasma were obtained from George King Biomedical, Inc., (Overland Park, Kans.). Monoclonal antibody to the heavy chain of FVIII (F8) coupled to CL4B-sepharose was used and may be prepared by known methods. Activated partial thromboplastin (Automated APTT reagent) was purchased from General Diagnostics Organon Teknika Corporation (Durham, N.C.). Soybean trypsin inhibitor, phenylmethylsulfonylfluoride (PMSF) and aprotinin were purchased from Boehringer, Mannheim GmbH (Mannheim, Germany). Human α-thrombin was obtained from Sigma Chemical Co. (St. Louis, Mo.). Human APC was purchased from Enzyme Research Laboratories, Inc., (South Bend, Ind.). Dulbecco's modified eagle medium (DMEM), α-modification of Eagle's Medium (α-MEM) and methionine-free DMEM were obtained from Gibco BRL (Gaithersburg, Md.). Fetal bovine serum was purchased from PAA Laboratories Inc., (Newport Beach, Calif.).

Plasmid construction. Site-directed oligonucleotide-mediated mutagenesis was performed by the gapped-heteroduplex procedure to introduce Arg336Ile (R336I) and/or Arg562Lys (R562K) mutations into the FVIII cDNA cloned into the expression vector pED6, as described previously. Pittman, D. D. et al., *Method in Enzymology* Vol. 222 (San Diego, Calif.; Academic Press, Inc.,) p. 236 (1993) and Toole, J. J. et al., *PNAS* (*USA*) 83:5939 (1986). The mutations were confirmed by extensive restriction endonuclease digestion and DNA sequence analysis. The resultant molecules were designated R336I or R562K and the double mutant, referred to herein as APC resistant FVIII, was designated R336I/R562K. In addition, a R336I/K338I double mutant was also constructed.

Analysis of synthesis and secretion. Plasmid DNA was transfected into COS-1 cells by the diethyl aminoethyl (DEAE)-dextran procedure as described. Pittman, D. D. et al., *Method in Enzymology* Vol. 222 (San Diego, Calif.; Academic Press, Inc.,) p. 236 (1993). Conditioned medium was harvested 60 hours post transfection in the presence of 10% heat-inactivated fetal bovine serum (FBS) for FVIII assay. Subsequently, cells were metabolically labeled with [$^{35}$S]-methionine as described before. Pittman, D. D. et al., *Method in Enzymology* Vol. 222 (San Diego, Calif.; Academic Press, Inc.,) p. 236 (1993). Labeled conditioned medium was harvested and immunoprecipitated with F8 antibody coupled to CL4B sepharose. Immunoprecipitated proteins from the conditioned medium were washed with PBS containing Triton X-100, resuspended 50 mM Tris-HCl pH 7.5, 150 mM NaCl, 2.5 mM $CaCl_2$ and 5% glycerol (buffer A), and were treated with or without 8.5 U/ml of thrombin at 37° C. for 1 hour. Samples were analyzed by sodium dodecyl sulfatepolyacrylamide gel electrophoresis (SDS-PAGE) under reducing conditions and visualized by autoradiography after fluorography by treatment with En3hance (Dupont; Boston, Mass.).

Analysis of APC cleavage of FVIII. Radiolabeled and immunoprecipitated FVIII was resuspended with buffer A and treated with 30 μg/ml of bovine APC in the presence of 100 μg/ml inosithin and 10 mM $CaCl_2$ at 37° C. for 1.5 hr. The resulting polypeptides were separated by SDS-PAGE and visualized by autoradiography as described above.

Generation of CHO cell lines and purification of FVIII In order to obtain large amounts of FVIII, stably transfected CHO cells lines were engineered containing DNA encoding the wild-type and APC resistant FVIII. The expression plasmids were digested with Cla1 and transfected into CHO cells using the lipofection method. Pittman, D. D. et al., *Method in Enzymology* Vol. 222 (San Diego, Calif.; Academic Press, Inc.,) p. 236 (1993). Conditioned media were applied to a column of F8 antibody coupled CL-4B sepharose. The bound FVIII was eluted in buffer containing 60% ethylene glycol and concentrated by dialysis against a 10% polyethylene glycol (MW 15K–20K) containing buffer. Fay, P. J. et al., *J. Biol. Chem.* (in press) (1996). Concentrated samples were dialyzed against modified buffer A containing 5 mM $CaCl_2$ (buffer B). The FVIII clotting activity of the purified preparations were about 20 U/ml. The structure of purified proteins was evaluated by SDS-PAGE and silver staining (Bio-Rad Laboratories; Hercules, Calif.).

FVIII assay. FVIII activities were measured in a one stage clotting assay using FVIII deficient plasma as substrate. One unit of FVIII activity is the amount measured in 1 ml of normal human pooled plasma. For thrombin activation, conditioned medium was diluted into buffer A and incubated at room temperature with 1 U/ml thrombin. After incubation for increasing periods of time, aliquots were diluted and assayed for FVIII activity.

APC inactivation of FVIII. Purified FVIII samples diluted to 3 U/ml in buffer B were mixed with 100 μg/ml inosithin and human APC 100 ng/ml or buffer alone as a control. After increasing periods of time at 37° C., aliquots were diluted and the residual FVIII was determined.

Effect of APC resistant FVIII in the APC resistance assay. Twenty U/ml of purified FVIII was diluted with FVIII deficient plasma to 1 U/ml. These samples were tested by the commercialized APC resistance assay kit (Coatest APC Resistance; Chromogenix, Molndal, Sweden) according to the manufacturer.

Results

Figure 3:
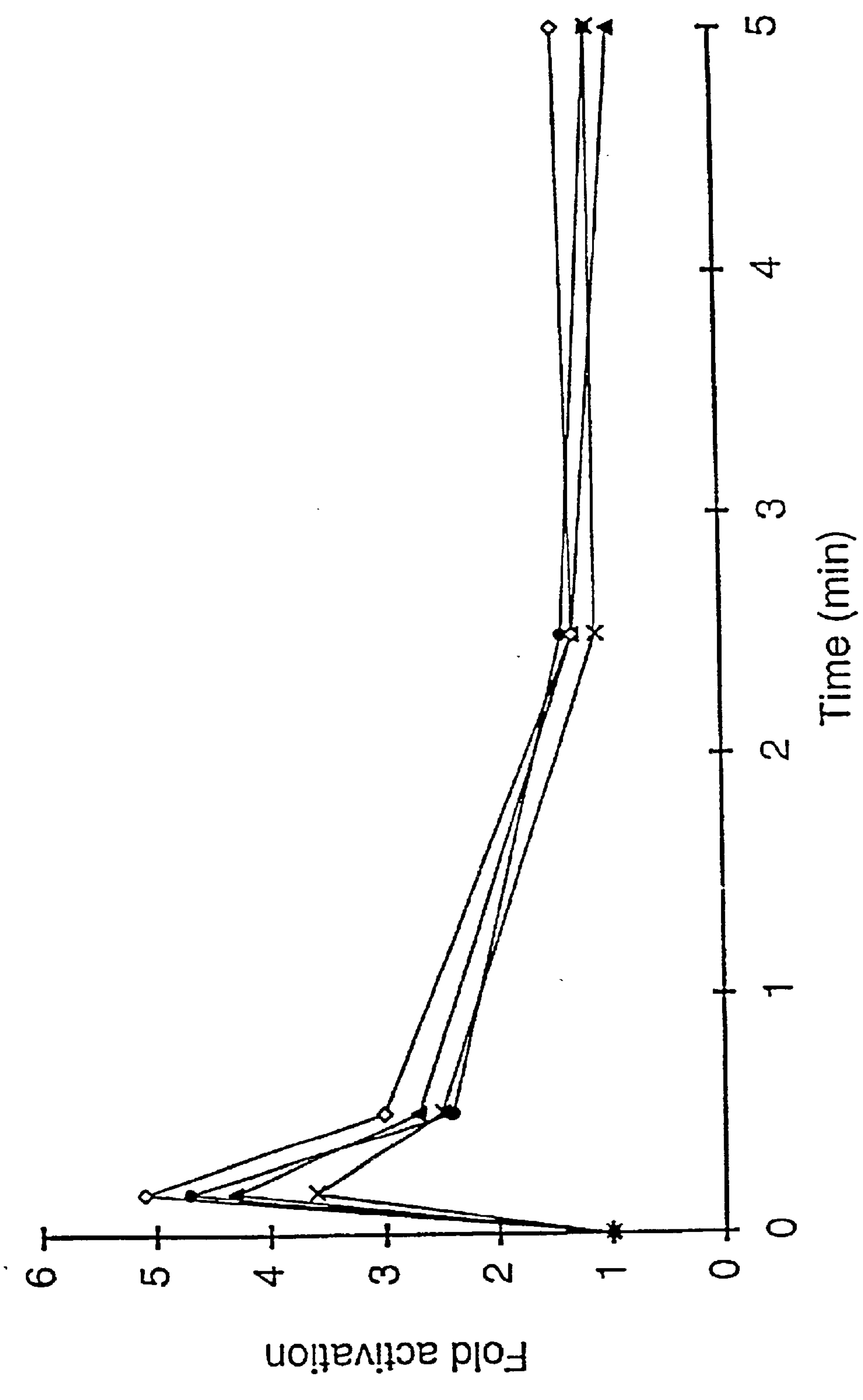
FIG. 3 is a graph showing the thrombin activation of APC resistant FVIII of the present invention and wild-type FVIII.
Figure 4A:
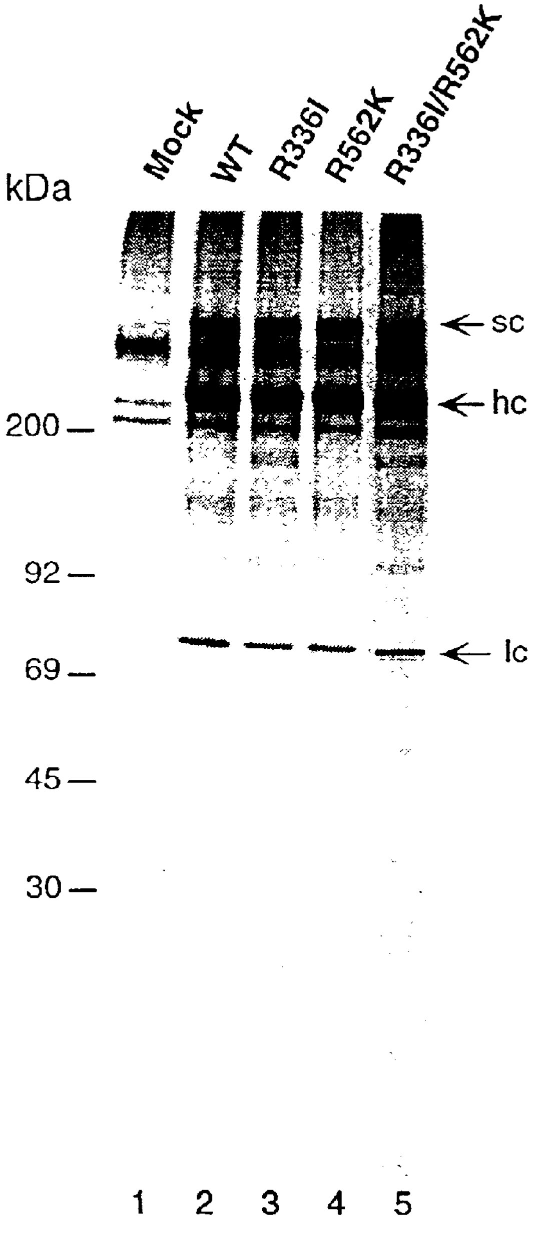
FIGS. 4A and 4B are photographs of gels showing the expression and thrombin cleavage of the APC resistant FVIII of the present invention.
Figure 4B:
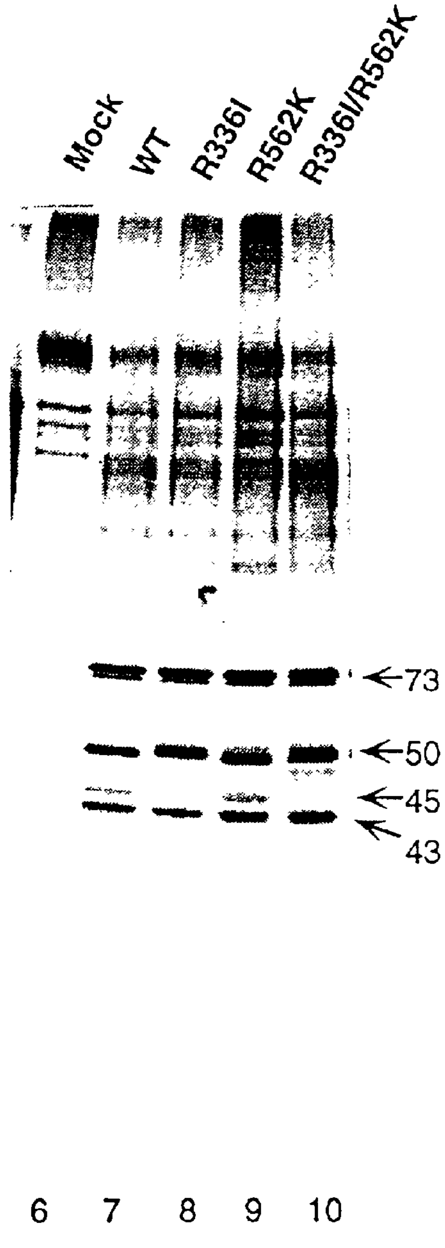

R336I, R562K, and R336I/R562K mutant FVIII molecules are efficiently secreted with FVIII activity similar to wild-type FVIII. The activity and secretion of FVIII mutants were measured by transient DNA transfection of COS-1 monkey cells. The FVIII clotting activity in the conditioned medium demonstrated that all mutants had FVIII activity similar to wild-type FVIII, approximately 300 mU/ml (see Table 1). Thrombin activation of the conditioned medium samples indicated that there was no difference in the rate of thrombin activation and decay of procoagulant activity. As shown in FIG. 3, all samples were immediately activated (3–5 fold) at 10 seconds after thrombin addition and were immediately inactivated. In FIG. 3, the symbols represent wild-type FVIII (X), R336I (•), R562K (◇) and R336I/R562K (▲). To measure FVIII secretion, transfected cells were metabolically labeled with [$^{35}$S]-methionine for 2 hr and then chased for 4 hr in medium containing excess unlabeled methionine. The secreted proteins were analyzed by immunoprecipitation of labeled conditioned medium. As shown in FIG. 4A, wild-type FVIII and all mutants were secreted at similar levels as a 300 kDa single chain and a 200 kDa heavy chain and an 80 kDa light chain. As shown in FIG. 4B, thrombin cleavage for all molecules generated the light chain migrating at 73 kDa and the heavy chain derived fragments corresponding to the 50 kDa A1-domain and 43 kDa A2-domain as expected (FIG. 4B). In addition, for wild-type FVIII and R562K (FIG. 4B, lanes 7 and 9) there was some cleavage at residue 336 to yield a 45 kDa species. In contrast, R336I and R336I/R562K (FIG. 4B, lanes 8 and 10) mutants did not generate the 45 kDa species, indicating that isoleucine mutation at residue 336 is resistant to cleavage by excess thrombin. For FIGS. 4A and 4B, the molecular size markers are shown on the left, "Mock" represents cells that did not receive DNA, and sc, hc and lc represent single chain, heavy chain and light chain, respectively.

TABLE 1

FVIII Clotting Activity in Conditioned Medium From Transfected COS-1 Cells

| | FVIII Clotting Activity (mU/ml) (n = 5) |
|---|---|
| Wild-type | 318.8 ± 36.3 |
| R336I | 306.4 ± 51.2 |
| R562K | 340.0 ± 44.8 |
| R336I/R562K | 308.4 ± 76.9 |

data represents mean ± SD

Figure 5A:
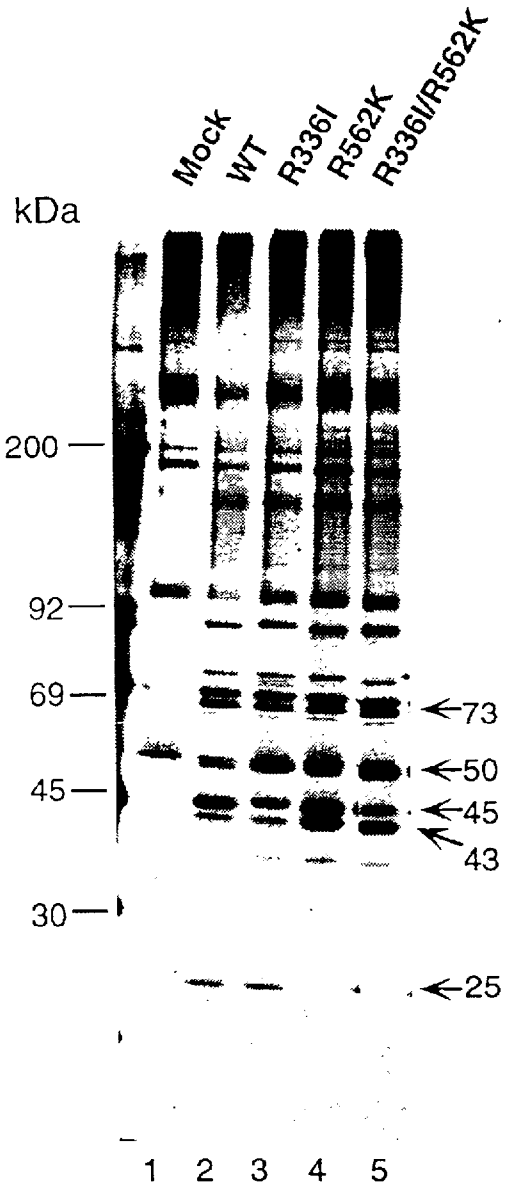
FIGS. 5A and 5B are photographs of gels showing APC cleavage of the APC resistant FVIII of the present invention.
Figure 5B:
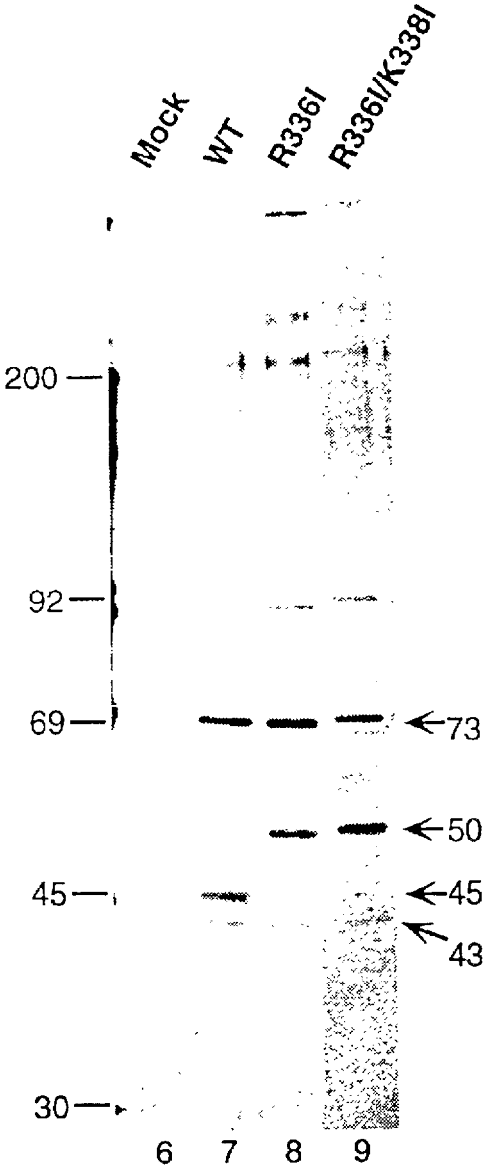

R562K is completely resistant and R336I is mostly resistant to APC cleavage at the mutated site. APC cleavage of FVIIIa was evaluated by treating [$^{35}$S]-methionine labeled immunoprecipitated FVIII with APC. Analysis of APC cleavage products of wild-type FVIII analyzed by SDS-PAGE on a 5–15% gradient gel detected the heavy chain fragments of 50 kDa and 45 kDa representing the A1-domain, and of 43 kDa representing the A2-domain, that were not present in the conditioned medium of cells that did not receive DNA. As shown in FIG. 5A, lane 2, a lower molecular weight product at 25 kDa was detectable, representing the carboxy-terminus of A2-domain. As shown in FIG. 5A, lane 3, R336I FVIII was partially resistant to cleavage at residue 336, as indicated by an increase in the 50 kDa and a reduction of the 45 kDa cleavage products compared to wild-type. The R336I displayed no change in the amount of the 25 kDa species indicating efficient cleavage at residue 562. As shown in FIG. 5A, lane 4, R562K mutant FVIII was resistant to cleavage at residue 562 as indicated by the increase in the 43 kDa fragment and loss of the 25 kDa fragment. However, the R562K mutant was efficiently cleaved at 336 as indicated by an intense 45 kDa fragment. APC treatment of the R336I/R562K double mutant yielded an increase in the 50 kDa and 43 kDa species, and the reduction of 45 kDa and loss of 25 kDa species compared to wild-type FVIII (see FIG. 5A, lane 5). The migration of the 45 kDa fragment derived from APC cleavage of the R336I mutant was slightly reduced upon analysis by SDS-PAGE on an 8% polyacrylamide gel (see FIG. 5B, compare lanes 7 and 8). In order to determine whether this mutant may be cleaved at the adjacent lysine at residue 338, an R336I and K338I double mutant was made by site-directed mutagenesis. The R336I/K338I mutant did not generate the 45 kDa fragment upon APC digestion (see FIG. 5B, lane 9). In FIGS. 5A and 5B, molecular size markers are shown on the left and "Mock" represents cells that did not receive DNA.

Figure 6:
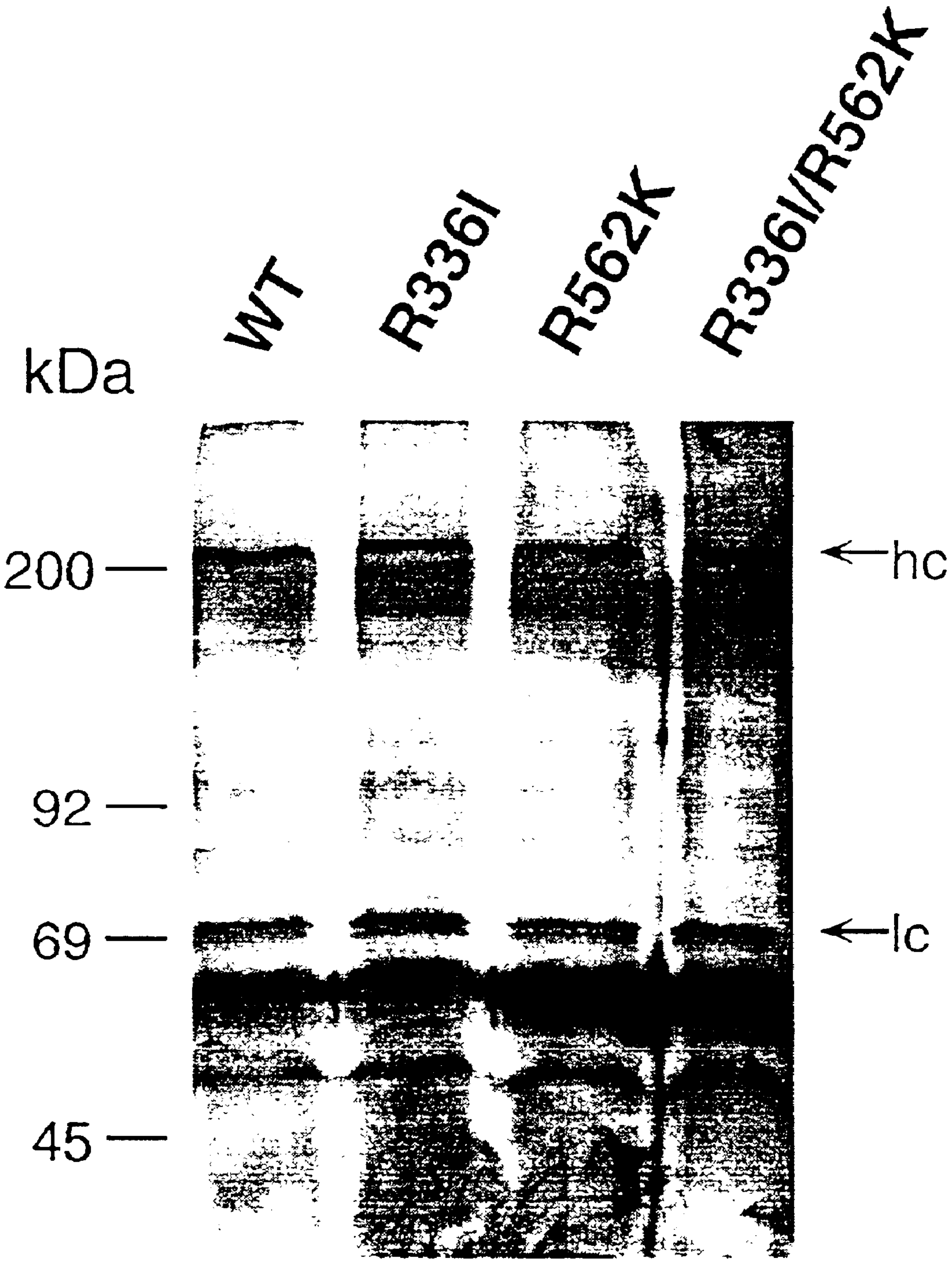
FIG. 6 is a photograph of a gel showing purified wild-type and APC resistant FVIII of the present invention.
Figure 7A:
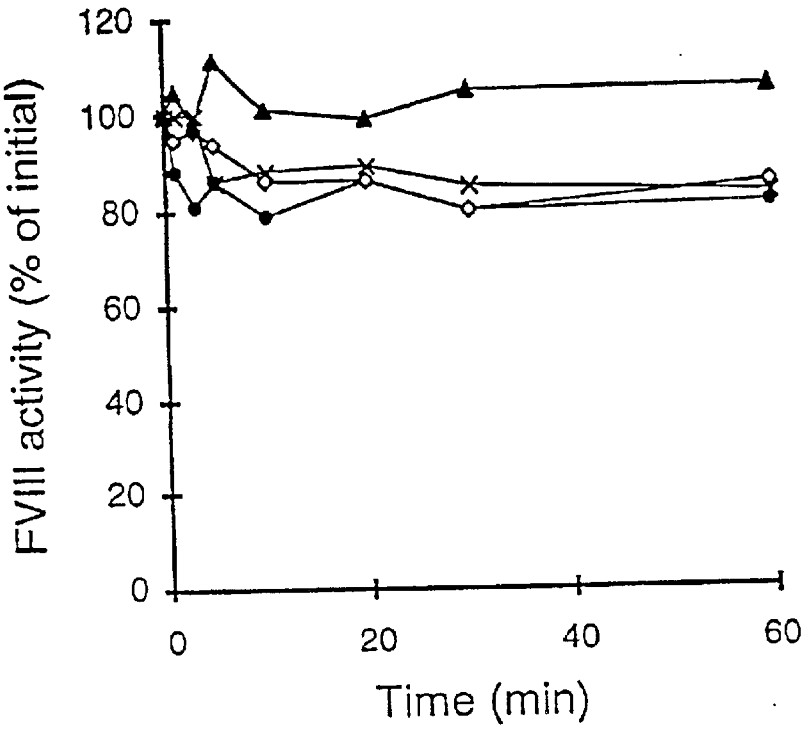
FIGS. 7A and 7B are graphs showing APC-mediated functional inactivation of wild-type and APC resistant FVIII of the present invention.
Figure 7B:
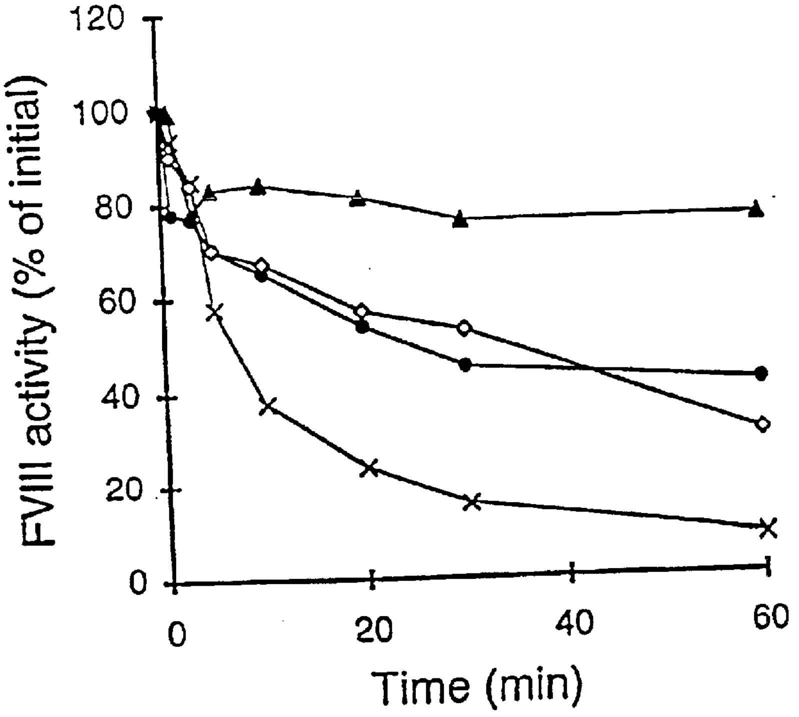

Mutagenesis at both Arg336 and Arg562 in FVIII are required for resistance to APC inactivation. von Willebrand Factor (vWF) inhibits APC inactivation of FVIII. Koedam, J. A. et al., *J. Clin. Invest.* 82:1236 (1988) and Fay, P. J. et al., *J. Biol. Chem.* 266:2172 (1991). Therefore, to study APC inactivation, stably transfected CHO cells that express wild-type and the APC cleavage site mutants FVIII molecules were engineered. Conditioned medium was collected for FVIII purification. As shown in FIG. 6, analysis of the purified proteins by SDS-PAGE under reducing conditions and silver staining demonstrated that all molecules have similar polypeptide compositions of heavy chain (hc) and light chain (lc) with minimal degradation and absence of vWF. These purified proteins were then analyzed for functional inactivation by APC. As shown in FIG. 7A, the activity of all samples, except the R336I/R562K (0̂) double mutant, were reduced to 80% after 10 min incubation at 37° C. in the absence of APC and were subsequently stable for 60 min thereafter. In the presence of APC, wild-type FVIII (X) had residual activity of 38% at 10 min and 8% at 60 min. In the presence of APC, the inactivation of R336I (•) and R562K (◇) single mutants were similar and both slower than wild-type FVIII. After 60 min 41% and 30% of initial activity remained for the R336I and R0̂K mutants, respectively. In contrast, the R336I/R562K (▲) double mutant was resistant to inactivation and retained 76% activity after 60 min. The results thus demonstrate that the R336I/R562K double mutant was mostly resistant and both single mutants were only partially resistant to APC inactivation.

Ability of APC resistance assay kit to detect APC resistant FVIII. Presently, a commercially available APC resistance assay kit (Coatest APC Resistance; Chromogenix, Molndal, Sweden) is used to screen the plasma of patients with thrombotic disease associated with the FV R506Q mutation. The ability of this kit to detect APC resistant FVIII was tested by reconstitution of FVIII deficient plasma with either purified wild-type or purified mutant FVIII. The APC resistance ratio was calculated by the measure of the clotting time in the presence of APC divided by the clotting time in the absence of APC (see Table 2). Only the R336I/R562K double mutant demonstrated a lower APC resistance ratio than 2, a value indicative of an APC resistance phenotype. Svensson, P. J. et al., *N. Engl. J. Med.* 336:517 (1994).

TABLE 2

APC-Resistance Ratio of Wild-Type FVIII and Mutants in the Commercialized Assay Kit

| | APC-Resistance Ratio (n = 3) |
|---|---|
| Wild-type | 2.13 ± 0.06 |
| R336I | 2.10 ± 0.00 |
| R562K | 2.13 ± 0.06 |
| R336I/R562K | 1.73 ± 0.06 |

data represents mean ± SD

Discussion

All mutants were efficiently secreted from COS-1 cells with a FVIII activity similar to wild-type FVIII. Analysis of APC cleavage was performed by [$^{35}$S]-methionine labeling of protein and analysis of FVIII in the conditioned medium after immunoprecipitation. The R336I mutant was partially resistant to cleavage at residue 336, but was sensitive to cleavage at Arg562. On the other hand, the R562K mutant was completely resistant to cleavage at residue 562, but was sensitive to cleavage at Arg336. These results indicate that either single mutation at Arg336 or Arg562 affects cleavage at the mutated site and that there is not a required order for APC cleavage at these two sites in FVIII. The double mutant R336I/R562K was partially resistant to cleavage at residue 336 and completely resistant at residue 562. The cleavage of R336I likely occurred at an adjacent residue, Lys 338, since a double mutant R336I/K338I was completely resistant to cleavage at this site. These results show that APC cleavage of FVIII can be ragged, i.e. it does not have a stringent spacing requirement for cleavage.

Analysis of the kinetics of APC cleavage in FVIII indicated that Arg562 was preferentially cleaved compared to Arg336 and this initial cleavage most closely correlated with the loss of cofactor activity. Fay, P. J. et al., *J. Biol. Chem.* 266:20139 (1991) The slower inactivation of the R562K single mutant as a consequence of cleavage resistance at residue 562 is consistent with the hypothesis, and that the resultant inactivation was due to cleavage at Arg336. However, the R336I single mutant was only partially inactivated by cleavage at Arg562. It has been shown that both single cleavage site mutants were inactivated at similar rates under the conditions described herein. Assuming that cleavage at Arg336 and Arg562 occur at the same time, the effect of cleavage at either Arg336 or Arg562 for inactivation of FVIII appear to be similar. The rapid inactivation of wild-type FVIII may be due to synergistic roles of cleavage at Arg336 and Arg562 for inactivation of FVIII.

At present, there are no reports describing patients with mutations in the APC cleavage sites of FVIII. To evaluate whether these mutations would have an APC resistance phenotype, the APC resistant FVIII molecules were tested in the commercially available APC resistance assay kit (Coatest APC Resistance; Chromogenix, Molndal, Sweden). Only the R336I/R562K double mutant demonstrated a lower APC-resistance ratio. This assay kit can not therefore, detect either single APC cleavage site mutants of FVIII. In contrast to FVIII, both FV APC single cleavage site mutants, Arg306Gln and Arg506Gln, showed reduced APC-resistance ratios in this assay. The results thus show that the commercially available APC resistance kit will not detect FVIII APC resistant mutants unless both APC cleavages are inhibited.

EXAMPLE 3

Preparation and Analysis of Inactivation Resistant Factor VIII

Experimental Procedures

Materials. Anti-heavy chain factor VIII monoclonal antibody (F-8), F-8 conjugated to CL-4B Sepharose and purified recombinant factor VIII protein were obtained from Genetics Institute Inc. (Cambridge, Mass.). Anti-human vWF horseradish peroxidase(HRP)-conjugated rabbit antibody was obtained from Dako Corp. (Carpinteria, Calif.). Anti-light chain factor VIII monoclonal antibodies, ESH-4 and ESH-8, were obtained from American Diagnostica, Inc., (Greenwich, Conn.). Factor VIII-deficient and normal pooled human plasma were obtained from George King Biomedical, Inc. (Overland Park, Kans.). Activated partial thromboplastin (Automated APTT reagent) and $CaCl_2$ were obtained from General Diagnostics Organon Teknika Corporation (Durham, N.C.). Human thrombin, soybean trypsin inhibitor, phenylmethylsulfonylfluoride and aprotinin were obtained from Boehringer, Mannheim GmbH (Mannheim, Germany). O-phenylendiamine dihydrochloride (OPD) was obtained from Sigma Chemical Co. (St. Louis, Mo.). [$^{35}$S] methionine(>1000 Ci/mmol) was obtained from Amersham Corp. (Arlington Heights, Ill.). En$^3$Hance was obtained from Dupont (Boston, Mass.). Fetal bovine serum was obtained from PAA Laboratories Inc. (Newport Beach, Calif.). Dulbecco's modified Eagle's medium (DMEM), methionine-free DMEM, OptiMEM, Biotin N-hydroxy succinimide ester, and streptavidin-horseradish peroxidase conjugate were obtained from Gibco BRL (Gaithersburg, Md.).

Plasmid mutagenesis. Mutagenesis was performed within the mammalian expression vector $pMT_2$(37) containing the FVIII cDNA($pMT_2$VIII). Mutant plasmids were generated through oligonucleotide site-directed mutagenesis utilizing the polymerase chain reaction (PCR). For a detailed description of oligonucleotide-directed mutagenesis, see Smith, M., *Annu. Rev. Genet.* 19:423 (1985).

Construction 1—90/73 R740K. Vector $pMT_2$90/73 was used as the DNA template. The 90/73 construct is described in Nesheim, M. et al., *J. Biol. Chem.* 266: 17815–17820 (1991) and Pittman, D. et al., *Blood* 70, Abstract No. 392 (1987). Generally, the 90/73 construct is wild-type FVIII cDNA sequence in which the B-domain and the vWF binding site (acidic region of the light chain) have been deleted (del 741–1689). Oligonucleotide-directed mutagenesis was used to create a PCR fragment, KpnI/R740K/ApaI, and was ligated into KpnI/ApaI digested $pMT_2$90/73.

Construction 2—90/b/73 R740K. Vector $pMT_2$VIII was used as the DNA template. Oligonucleotide-directed mutagenesis was used to create a PCR fragment, KpnI/b/1689 MluI (where b represents a DNA sequence encoding for amino acid residues 741 to 793 of the wild-type sequence followed by an MluI site predicting amino acids threonine and arginine at residues 794 and 795/1689), which was ligated into KpnI/MluI digested vector $pMT_2$ VIII/1689/MluI. The following amino acid sequence (and nucleotide sequence encoding same) is the preferred amino acid sequence spacer, wherein residue 794 may be threonine (SEQ ID NOS: 1 and 2) or leucine and is preferably threonine:

```
5' AGC TTC TCC CAG AAT TCA AGA CAC CCT AGC
    S   F   S   Q   N   S   R   H   P   S

ACT AGG CAA AAG CAA TTT AAT GCC ACC ACA ATT
 T   R   Q   K   Q   F   N   A   T   T   I

CCA GAA AAT GAC ATA GAG AAG ACT GAC CCT TGG
 P   E   N   D   I   E   K   T   D   P   W

TTT GCA CAC AGA ACA CCT ATG CCT AAA ATA CAA
 F   A   H   R   T   P   M   P   K   I   Q

AAT GTC TCC TCT AGT GAT TTG TTG ATG CTC TTG 3'
 N   V   S   S   S   D   L   L   M   L   L
```

Construction 3—90/b/73 R740A. Vector 90/b/73 was used as the DNA template (wherein b is described above and encodes threonine at residue 794). Oligonucleotide-directed mutagenesis was used to create a PCR fragment, KpnI/R740A/b/ApaI, which was ligated into KpnI/ApaI digested $pMT_2$90/73.

Construction 4—90/b/73 R740A/R1689A (DM1). Vector 90/b/73 R740A was used as the DNA template (wherein b is described above and encodes leucine at residue 794). Oligonucleotide-directed mutagenesis was used to create PCR fragment, KpnI/R740A/b/R1689A/ApaI, which was ligated into KpnI/ApaI digested $pMT_2$90/73.

Construction 5—90/b/73 R336I/R740A (DM2). Vector $PMT_2$VIII/R336I was digested with SpeI and KpnI. The fragment was ligated into SpeI/KpnI digested 90/b/73 R740A (wherein b is described above and encodes threonine at residue 794).

Construction 6—90/b/73 R336I/R562K/R740A (IR8). Vector $PMT_2$VIII/R562K was digested with BglII and KpnI. The BglII/R562K/KpnI fragment was ligated into BglII/KpnI digested 90/b/73 R336I/R740A (wherein b is described above and encodes threonine at residue 794).

The plasmid containing the wild-type FVIII cDNA sequence was designated FVIII WT. All plasmids were purified by centrifugation through cesium chloride and characterized by restriction endonuclease digestion and DNA sequence analysis.

DNA Transfection and Analysis. Plasmid DNA was transfected into COS-1 cells by the DEAE-dextran method. Conditioned medium was harvested at 64 hours post-transfection in the presence of 10% fetal bovine serum. FVIII activity was measured by one-stage APTT clotting assay on a MLA Electra 750. Protein synthesis and secretion were analyzed by metabolically labeling cells at 64 hours post-transfection for 30 minutes with [$^{35}$S]-methionine (300 mCi/ml in methionine-free medium), followed by a chase for 4 hours in medium containing 100 fold excess unlabeled methionine and 0.02% aprotinin. Cell extracts and conditioned medium containing labeled protein were harvested. WT and mutant FVIII proteins were immunoprecipitated from equal proportions of cell extract and conditioned medium with F-8 coupled to CL4B Sepharose. Immunoprecipitates were washed and resuspended in Laemmli sample buffer. Samples were analyzed by electrophoresis on a reducing SDS-low bis-8% polyacrylamide gel. The gels were treated with En$^3$Hance and the proteins visualized by autoradiography.

Protein purification. Partially purified IR8 protein was obtained from 200 mls of conditioned medium from transiently transfected COS-1 cells by immunoaffinity chromatography. Partially purified FVIII WT protein was obtained from 200 mls of conditioned medium from stably transfected CHO cells and immunoaffinity purified in the same manner. The proteins eluted into the ethylene glycol-containing buffer were dialyzed and concentrated against a polyethylene glycol (MW ~15–20,000)-containing buffer and stored at −70° C.

FVIII activity assay. FVIII activity was measured in a one-stage APTT clotting assay by reconstitution of human FVIII-deficient plasma. For thrombin activation, protein samples were diluted into 50 mM Tris-HCl pH 7.5, 150 mM NaCl, 2.5 mM $CaCl_2$ and 5% glycerol, and incubated at room temperature with 1 U/ml thrombin. After incubation for increasing periods of time, aliquots were diluted and assayed for FVIII activity. One unit of FVIII activity is the amount measured in 1 ml of normal human pooled plasma.

FVIII antigen determination. FVIII antigen was quantified using a sandwich ELISA method utilizing anti-light chain antibodies ESH-4 and ESH-8. Purified recombinant FVIII protein was used as a standard.

Results

Figure 8:
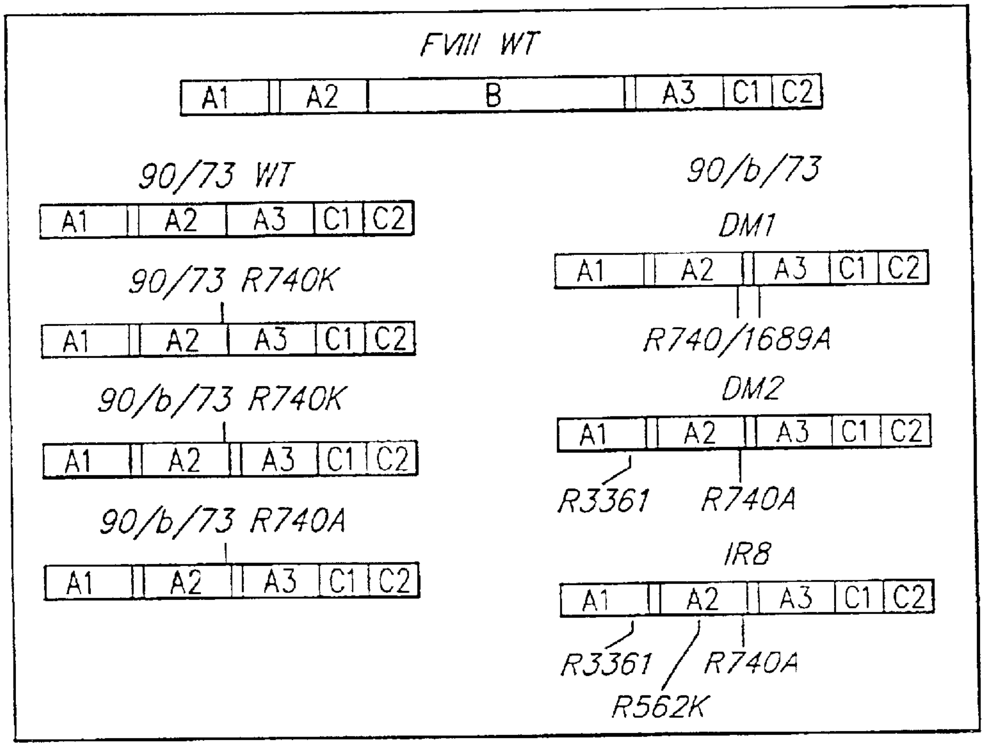
FIG. 8 is a diagram of the domain structure of the single-chain inactivation resistant FVIII of the present invention.
Figure 9:
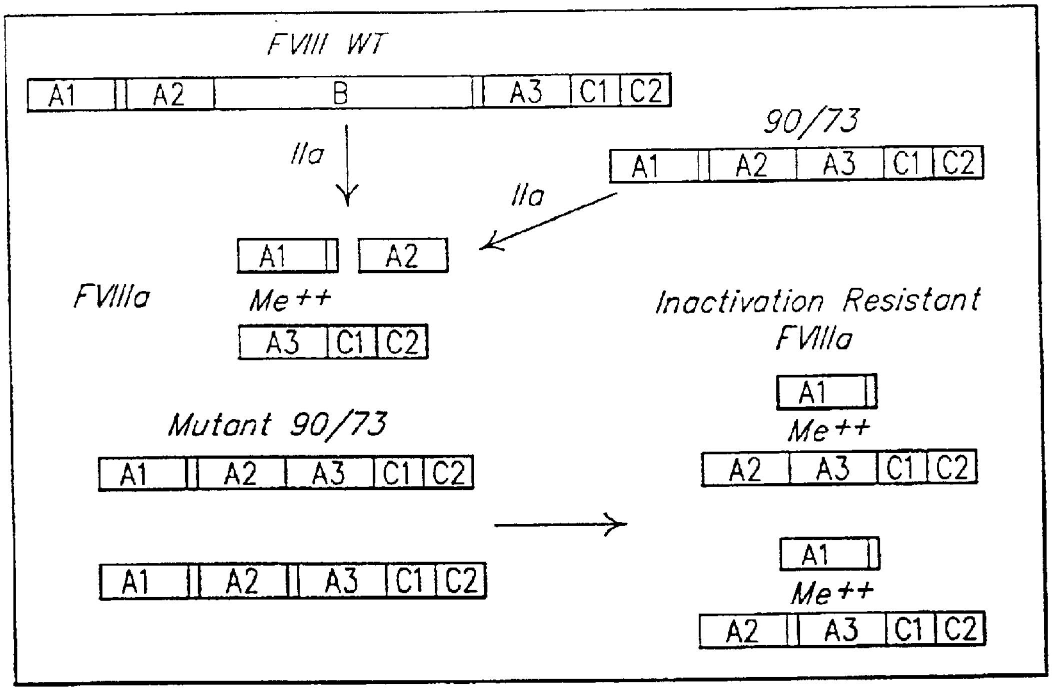
FIG. 9 is a diagram of the domain structure of the inactivation resistant heterodimer FVIII protein of the present invention.

Generation of FVIII inactivation resistance. All of the above constructs are based upon 90/73, wherein the B-domain (residues 795 to 1647) and the vWF binding site (residues 1648 to 1688, also referred to as the acidic region of the amino terminus of the light chain), have been deleted. Nesheim, M. et al., *J. Biol. Chem.* 266: 17815–17820 (1991) and Pittman, D. et al., *Blood* 70, Abstract no. 392 (1987). FIG. 8 sets forth the domain structures of wild-type FVIII and the above constructs as well as the mutations at the APC and thrombin cleavage sites. As described herein and in FIG. 8, "b" represents the amino acid sequence spacer which is of a sufficient length to allow the protein to be activated by thrombin to achieve a heterodimer, wherein the A2-domain remains covalently associated with the light chain. In a preferred embodiment, the amino acid sequence spacer is preferably the amino portion of the wild-type B-domain, i.e. amino acid residues 741 to 793 followed by an MluI site (for cloning purposes) predicting amino acids threonine or leucine, preferably threonine, at residue 794 and arginine at 795/1689.

FIG. 8 sets forth a model of activation of the constructs of the present invention. Wild-type FVIII and the mutant 90/73 both achieve a heterotrimer upon thrombin activation. When an amino acid sequence spacer is introduced between the A2- and A3-domains of 90/73 containing a mutation at the thrombin cleavage site (del795–1688/Arg336Iso/Arg562Lys/Arg740 Ala), upon activation with thrombin, cleavage only occurs after Arg372, generating a FVIIIa heterodimer. This novel FVIII protein designated IR8, maintains stable activity following thrombin activation.

Figure 10:
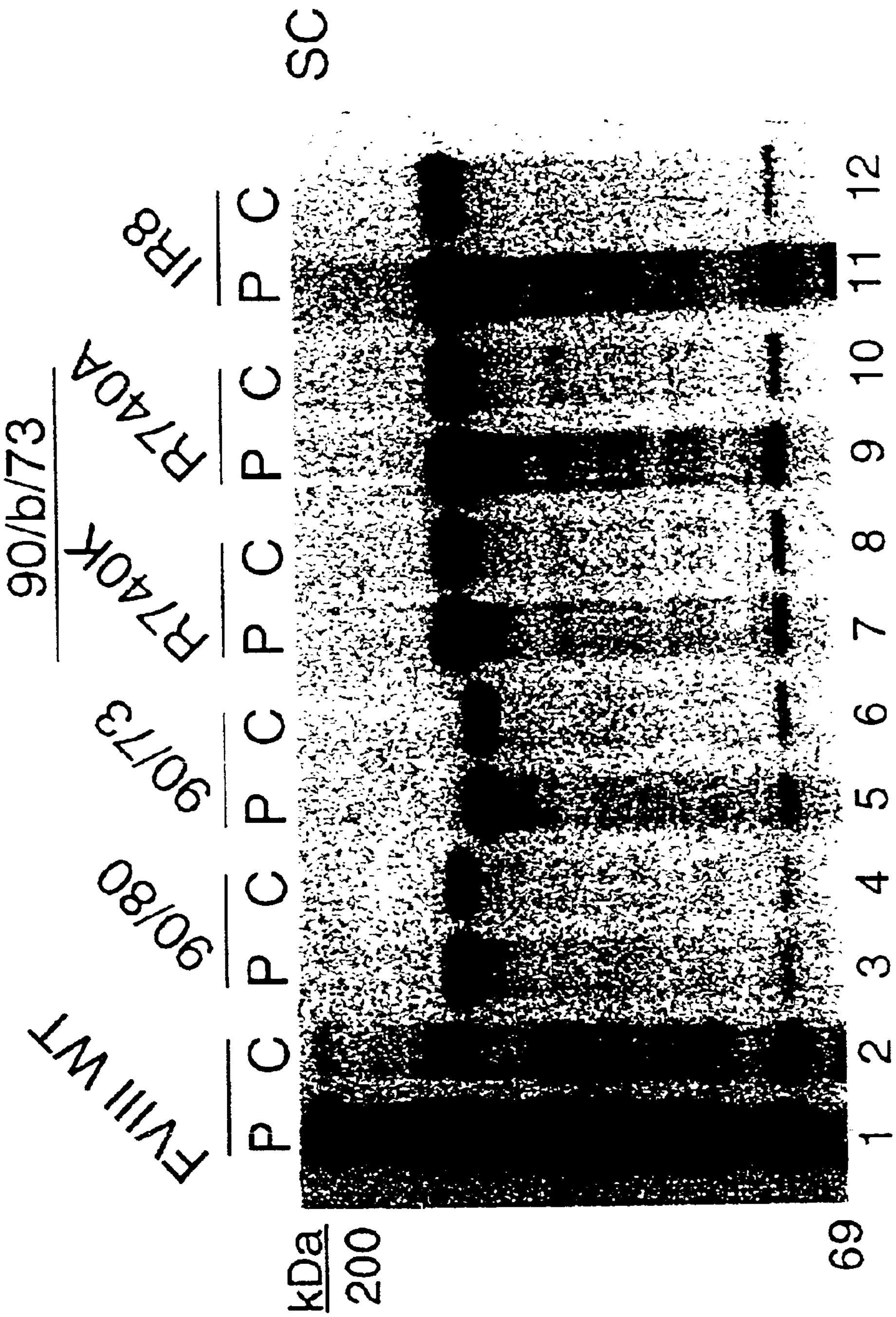
FIG. 10 is a photograph of a gel showing relative synthesis and secretion levels of the inactivation resistant FVIII of the present invention.
Figure 11:
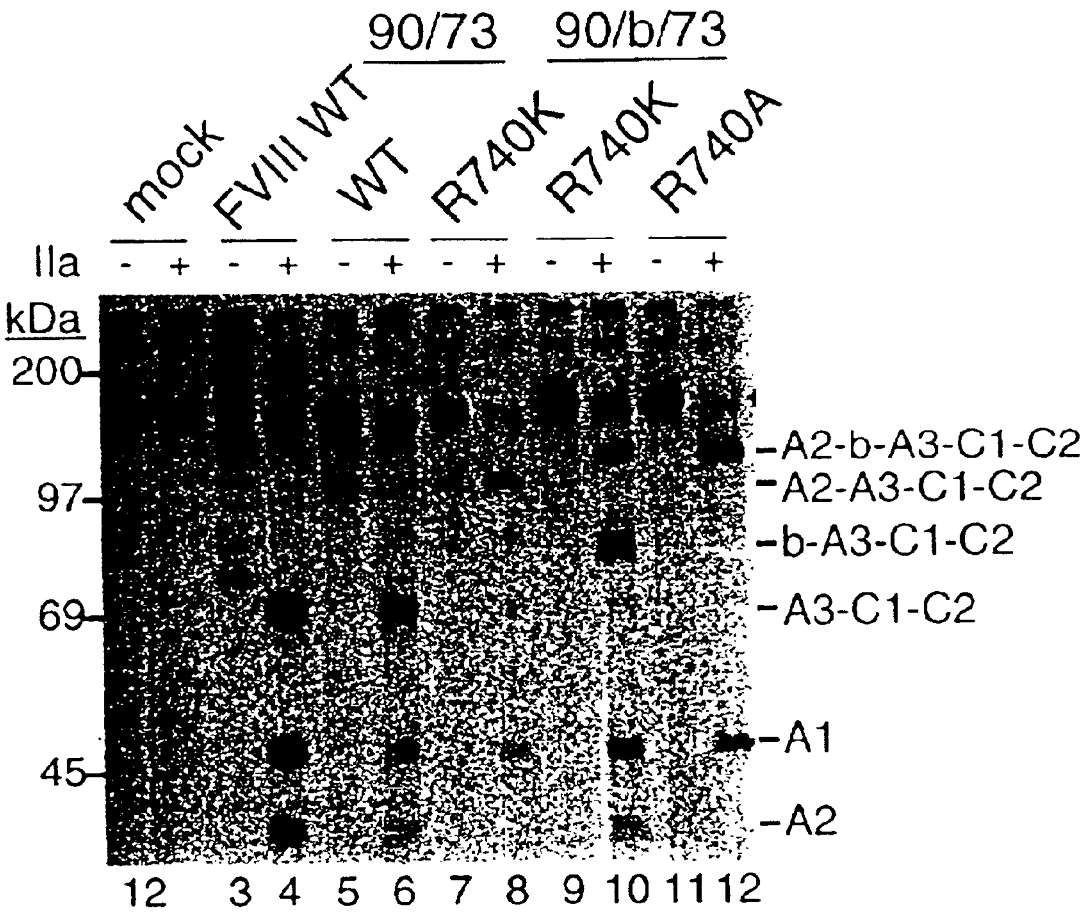
FIG. 11 is a photograph of a gel showing the cleavage patterns of the inactivation resistant FVIII of the present invention.

Synthesis and Secretion of IR8. FVIII WT and the various inactivation-resistance mutants were compared by transient DNA transfection of the cDNA expression vectors into COS-1 monkey cells. At 60 hours following transfection, the rates of synthesis were analyzed by immunoprecipitation of cell extracts from [$^{35}$S]-methionine pulse-labeled cells. Intracellular FVIII WT was detected in its single chain form and migrated at approximately 250 kDa (FIG. 10, lane 1). The mutant 90/80 is a BDD FVIII mutant (del741–1648) previously characterized, that migrates at ~170 kDa and demonstrates an increased intensity from pulse-labeled cell extracts consistent with increased efficiency of synthesis (FIG. 10, lane 3). 90/73 migrates slightly faster due to the additional deletion of the residues of the acidic region (FIG. 10, lane 5). All the 90/b/73 based constructs including IR8 exhibited similar band intensity to the 90/80 and 90/73 constructs suggesting that the multiple missense mutations did not interfere with efficient protein synthesis. Additional bands within the cell extract are not observed in mock cell extract immunoprecipitated with an anti-FVIII specific antibody and represent both FVIII specific proteins and co-immunoprecipitating intracellular proteins. Following a 4 hour chase period, the majority of FVIII WT is lost from the cell extract (FIG. 10, lane 2) and can be recovered from chase conditioned medium in its 280 kDa single chain, 200 kDa heavy chain and 80 kDa light chain forms (FIG. 10, lane 3). Although all of the BDD and inactivation-resistance mutants demonstrated significant amounts of their primary translation products remaining within the cell extract following the 4 hour chase (FIG. 10, lanes 4, 6, 8, 10, 12), they were all recovered from the chase conditioned medium as single chain species (FIG. 11, lanes 5, 7, 9, 11, 13). Therefore the various alterations of the FVIII construct did not have significant impact on secretion.

Structural stability of IR8 following thrombin cleavage. The labeled FVIII proteins immunoprecipitated from the chase conditioned medium were incubated with thrombin (1 U/ml) for 30 minutes prior to SDS-PAGE analysis. FVIII WT was efficiently cleaved into a heterotrimer of fragments consisting of a 50 kDa A1 subunit, 43 kDa A2 subunit and 73 kDa thrombin-cleaved light chain, A3-C1-C2 (FIG. 11, lane 4). 90/73 WT was also cleaved into a heterotrimer of subunits similar to FVIII WT (FIG. 11, lane 6) consistent with previous observations and depicted in FIG. 1A. 90/73 Arg740Lys generated a heterodimer of thrombin-cleaved subunits consistent with a 50 kDa A1 subunit and an A2-A3-C1-C2 fused light chain (FIG. 11, lane 8). 90/b/73 Arg740Lys demonstrated thrombin cleavage fragments consistent with 2 heteromeric species, a 50 kDa A1/120 kDa A2-b-A3-C1-C2 heterodimer, as well as a 43 kDa A2 subunit and an ~85 kDa fragment consistent with a b-A3-C1-C2 fused light chain (FIG. 11, lane 10). The appearance of the A2 subunit following incubation with thrombin suggested that Lys740 did not completely abrogate thrombin cleavage in the presence of the b spacer. With the more radical missense mutation to Ala740, a stable heterodimeric species was demonstrated (FIG. 11, lane 12). This stable heterodimeric structure following thrombin cleavage was maintained for IR8 with additions of the missense mutations Arg336Iso and Arg562Lys (FIG. 11, lane 14).

Figure 12:
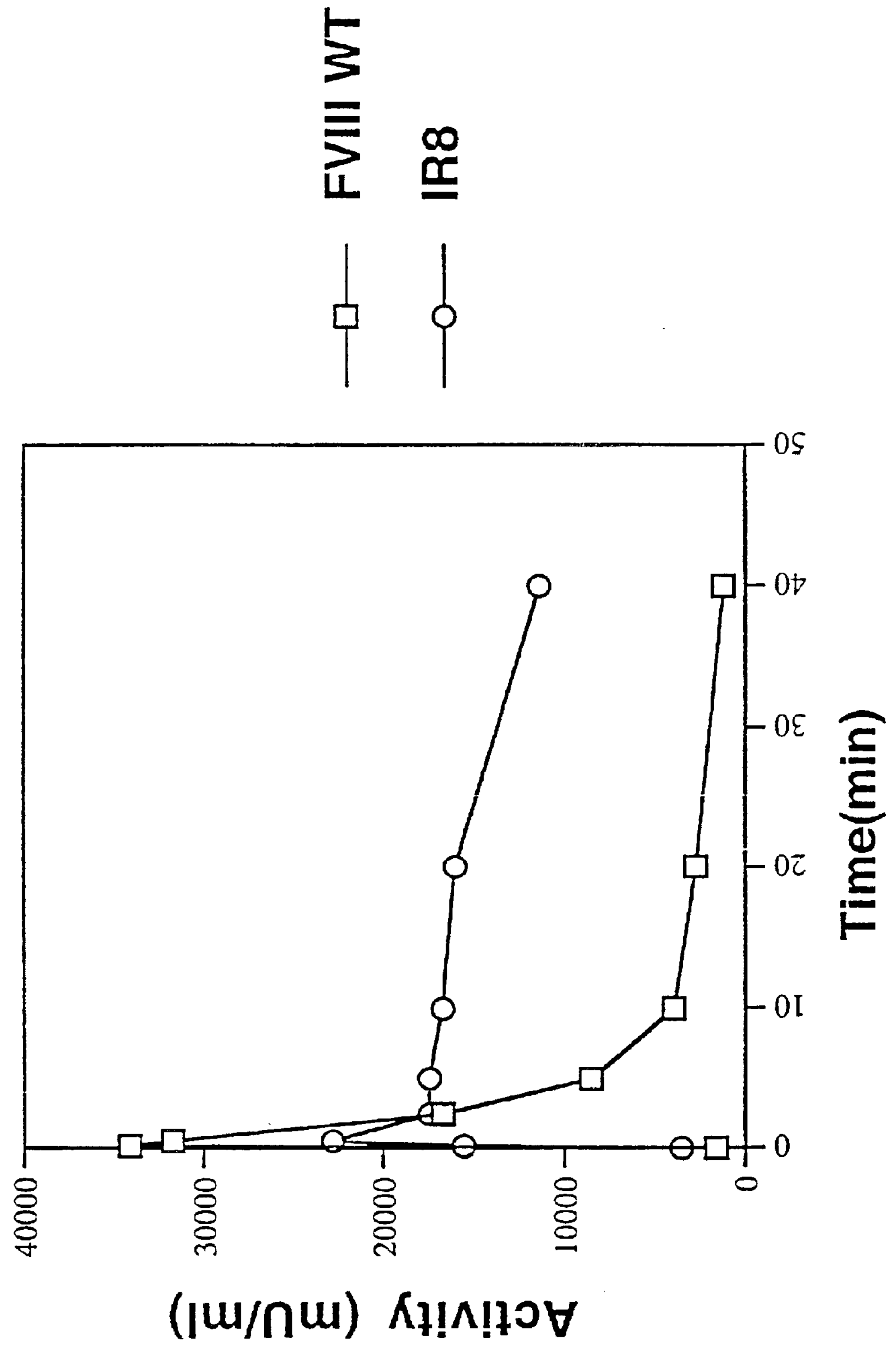
FIG. 12 is a graph showing the functional activation and inactivation of the inactivation resistant FVIII of the present invention as compared to wild-type FVIII.

Functional stability of IR8 following thrombin activation. Having demonstrated the structural integrity of the IR8 heterodimer upon thrombin cleavage, the functional consequence of this modification on activation and inactivation was examined in an in vitro functional assay. Immunoaffinity purified FVIII WT and IR8 were incubated with thrombin and assayed for FVIII activity by a one stage APTT clotting assay. An example of the functional activation and inactivation is depicted in FIG. 12 and is typical of multiple repeat experiments. Under these conditions, FVIII WT was maximally activated within the first 10 seconds of incubation with thrombin, then rapidly inactivated over the next 5 minutes. IR8 did not reach peak activity until 30 seconds incubation with thrombin, suggesting a modestly reduced sensitivity to thrombin activation compared to FVIII WT. In addition, the peak activity for thrombin activated IR8 was lower (74.7+6.7% of peak thrombin activated FVIII WT activity, n=3), suggesting some reduced efficiency as a cofactor. However, IR8 demonstrated significant retention of peak activity over the first 10 minutes of incubation with thrombin (66.9+5.3% of peak IR8 activity, n=3), a period in which FVIII WT was almost completely inactivated. Although there is a gradual loss of peak IR8 activity with prolonged incubation with thrombin, IR8 still retained ~38% of peak activity after 4 hours incubation with thrombin.

Figure 13:
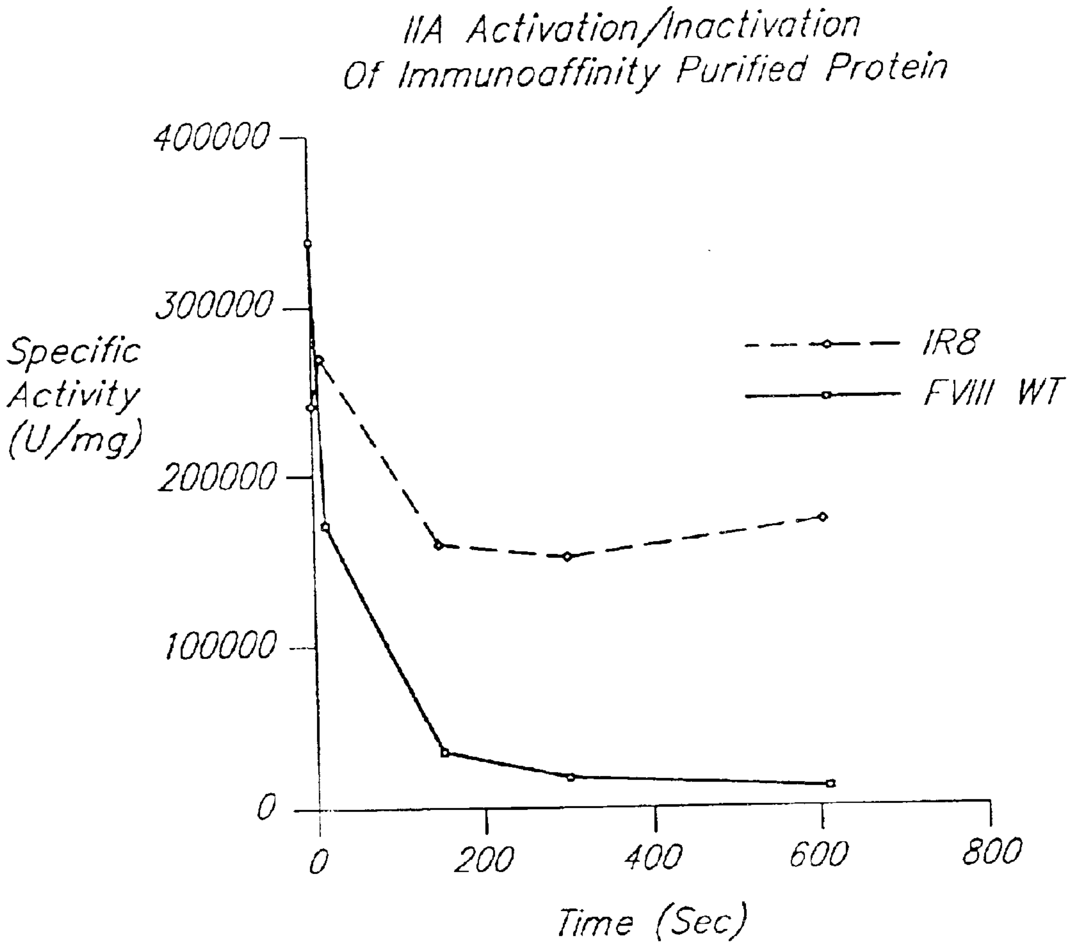
FIG. 13 is a graph showing the activation and reduced rate of inactivation of immunoaffinity purified inactivation resistant FVIII of the present invention as compared to wild-type FVIII.

IR8 demonstrates increased FVIII specific activity in vitro. Immunoaffinity purified FVIII WT and IR8 were assayed for FVIII activity utilizing a standard one stage APTT clotting assay, wherein the first time point was 10 seconds. Antigen determinations were made utilizing a FVIII light chain based ELISA. FIG. 13 shows the activation and reduced rate of inactivation expressed as specific activity. The specific activity values for IR8 were calculated based on a correction for its molecular weight. IR8 was observed to have a 5-fold increased specific activity compared to FVIII WT (102±43 vs. 18.6±7.4 U/mg of protein).

EXAMPLE 4

Inducible vWF-binding of Inactivation Resistant Factor VIII

Experimental Procedures

Immulon 2 microtiter wells (Dynatech Laboratories, Inc., Chantilly, Va.) were coated with FVIII antibody at a concentration of 2 μg/ml overnight at 4° C. in a buffer of 0.05 M sodium carbonate/bicarbonate pH 9.6. Wells were washed with TBST (50 mM Tris HCUpH 7.6, 150 mM NaCl, 0.05% Tween 20) then blocked with 3% bovine serum albumin (BSA) in TBST. Protein samples were diluted in TBST, 3% BSA, 1% factor VIII-deficient human plasma +/− ESH8 (molar ratio of ESH8:FVIII protein=2:1). Samples were incubated for 2 hours at 37° C. in 1.7 ml microfuge tubes. Samples were then incubated for an additional 2 hours in the blocked and washed microtiter wells. Wells were then washed in TBST containing 10 mM $CaCl_2$. Anti-vWF-HRP antibody was diluted in TBST, 3% BSA, 10 mM $CaCl_2$ and incubated in the wells for 2 hours at 37° C. Following additional washing with TBST containing 10 mM $CaCl_2$, OPD substrate was added to the wells and incubated for 3 minutes. The color reaction was stopped with 2 M $H_2SO_4$ and the optical density (O.D.) read at 490 nm using an EL 340 automated microplate reader (Biotek Instruments Inc., Winooski, Vt.).

Results

Figure 14:
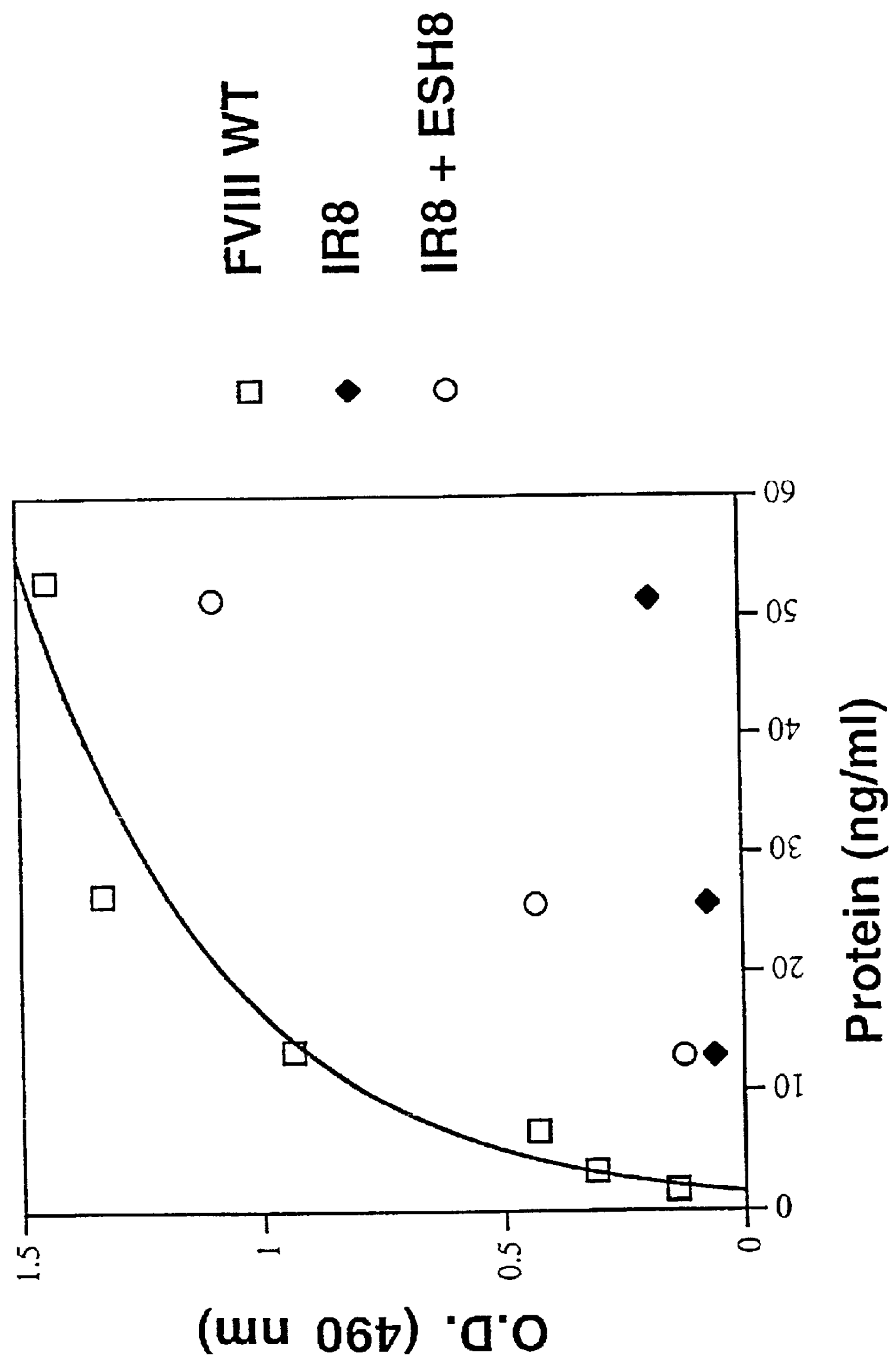
FIG. 14 is a graph illustrating the results of an ELISA assay demonstrating antibody-inducible vWF binding of the inactivation resistant FVIII of the present invention.

FIG. 14 shows the results of the FVIII-vWF binding ELISA. An anti-A2 domain trap was used. After a 4 hour incubation with FVIII-deficient plasma (1:100 dilution), binding was detected by perioxidase conjugated anti-vWFab. As shown in FIG. 14, a 10-fold lower binding affinity of IR8 to vWF is observed in the absence of ESH8 compared to wild-type FVIII, and a 2-fold lower binding affinity is observed in the presence of ESH8.

Figure 15:
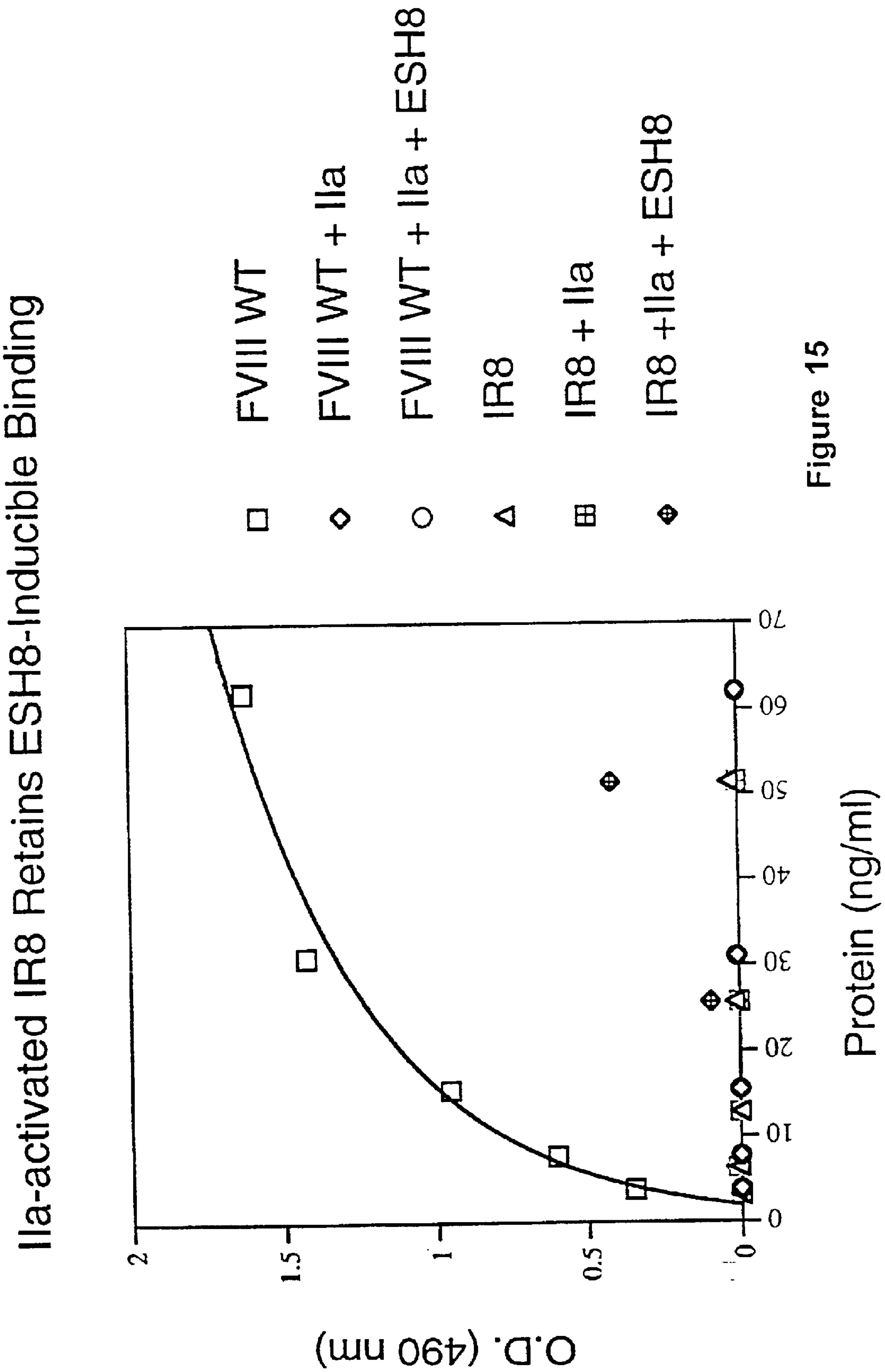
FIG. 15 is a graph illustrating the results of an ELISA assay demonstrating antibody-inducible vWF binding of the inactivation resistant FVIII of the present invention following thrombin activation.

FIG. 15 shows the results of the FVIII-vWF binding ELISA with thrombin (IIa) and/or ESH8. The same ELISA method was used however a 2-fold molar excess of ESH8 was employed as well as a 4 hour incubation with IIa (1 U/ml) in the presence of FVIII deficient plasma. As shown in FIG. 15, IR8 retains activity for vWF after thrombin activation suggesting that the heterodimer is intact after thrombin cleavage and ESH8 stabilizes the light chain confirmation such that it retains some affinity for vWF.

Since the binding assays described above utilize a "trap" antibody that only recognizes the A2-domain of FVIII, it will only detect FVIII-vWF complexes that recognize the A2-domain in association with the rest of the protein. Therefore, following the 4 hour incubation of the protein in the presence of excess thrombin, FVIII wild-type will not only have been fully activated but it will have also have been completely inactivated through A2 dissociation and/or further proteolytic cleavages, and will no longer associate with vWF in a complex that will be recognized by this assay. The inactivation resistant FVIII of the present invention thus retains inducible binding even following complete activation by thrombin.

Figure 16:
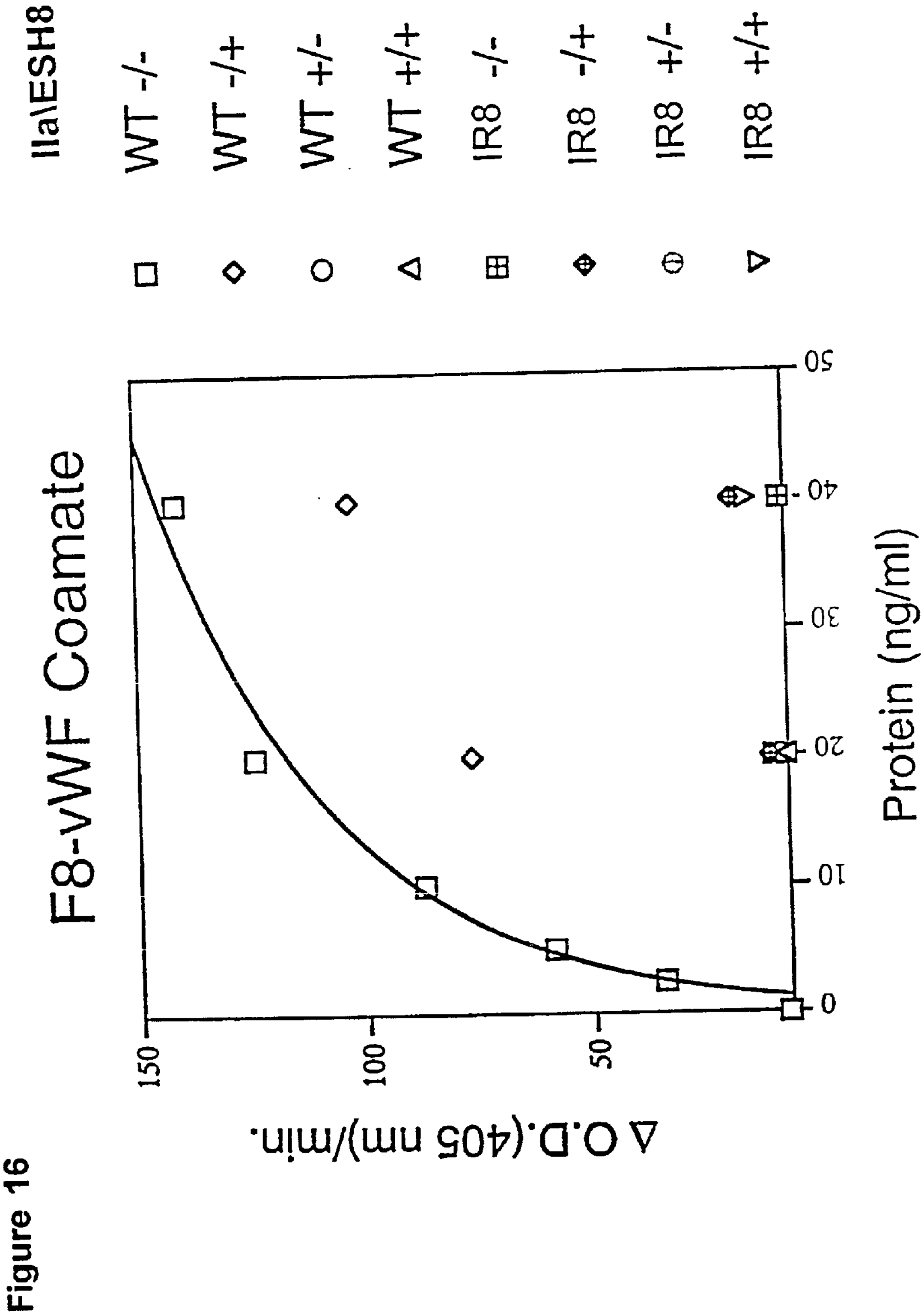
FIG. 16 is a graph illustrating the results of an ELISA assay demonstrating antibody-inducible vWF binding of the inactivation resistant FVIII of the present invention following thrombin activation, and retained FVIII activity.

It was also shown that the inducible vWF-binding form of the inactivation resistant FVIII of the present invention retained activity. In this assay, an anti-vWF antibody was used as the "trap" for the ELISA. The same incubation was performed in the presence and absence of thrombin and ESH8. Following immobilization of the FVIII-vWF complex on the plate, FVIII activity was measured using a chromogenic FVIII assay kit (Coamatic, Pharmacia Hepar, Franklin, Ohio) within the ELISA wells. As shown in FIG. 16, following activation by thrombin, no demonstrably active FVIII-vWF complexes were observed for FVIII wild-type. However, the inactivation resistant FVIII still had detectable activity under the same conditions. This suggests that following thrombin activation, the inactivation resistant FVIII is cleaved to a heterodimer of A1 in association with a modified light chain of A2-b-A3-C1-C2 that has ESH8-inducible binding to vWF, and retains FVIII activity.

The functional impact of this ESH8-induced IR8-vWF complex was also evaluated by assaying for FVIII activity via APTT (Table 3). In the absence of ESH8, immunoaffinity purified FVIII WT and IR8 demonstrated minimal loss of activity over a 4 hour incubation at 37° C. with FVIII-deficient plasma. In the presence of ESH8, FVIII WT activity was inhibited by approximately 70%, whereas IR8 retained 100% of its initial activity. These results suggest that inactivation of WT FVIII in the presence of ESH8 may be due to A2 subunit dissociation and IR8 is resistant to inactivation by ESH8 because it is not susceptible to A2 subunit dissociation.

TABLE 3

ESH8 Does Not Inhibit IR8 Activity In Presence Of vWF

| | % Of Initial Activity | |
|---|---|---|
| Protein | −ESH8 | +ESH8 |
| FVIII WT | 92 ± 3 | 29 ± 13 |
| IR8 | 101 ± 2 | 120 ± 27 |

EXAMPLE 5

Pharmaceutical Compositions and Use

Pharmaceutical Composition

The FVIII proteins of the present invention can be formulated into pharmaceutically acceptable compositions with parenterally acceptable vehicles and excipients in accordance with procedures known in the art. The pharmaceutical compositions of this invention, suitable for parenteral administration, may conveniently comprise a sterile lyophilized preparation of the protein which may be reconstituted by addition of sterile solution to produce solutions preferably isotonic with the blood of the recipient. The preparation may be presented in unit or multi-dose containers, e.g. in sealed ampoules or vials.

Such pharmaceutical compositions may also contain pharmaceutically acceptable carriers, diluents, fillers, salts, buffers, stabilizers, and/or other materials well known in the art. The term "pharmaceutically acceptable" means a non-toxic material that does not interfere with the effectiveness of the biological activity of the active ingredient(s). The characteristics of the carrier or other material will depend on the route of administration.

The amount of FVIII protein in the pharmaceutical composition of the present invention will depend upon the nature and severity of the condition being treated, and on the nature of the prior treatments which the patient has undergone. Ultimately, the attending physician will decide the amount of protein with which to treat each individual patient. The duration of intravenous therapy similarly will vary, depending on the severity of the disease being treated and the condition and potential idiosyncratic response of each individual patient.

In addition, the nucleotide sequences encoding the FVIII proteins of the present invention may be associated with a gene therapy delivery system in accordance with procedures known in the art. Such delivery systems include, without limitation, adenoviral, retroviral and adeno-associated viral vectors, as well as liposomes and DNA-protein complexes. The sequences of the present invention are contained in or operatively-linked to such delivery systems in a manner which allows for transcription, e.g., through the use of sufficient regulatory elements. It will be appreciated that a variety of strategies and methodology for creating such gene therapy delivery systems are well known to those skilled in the art.

Methods of Use

Pharmaceutical compositions containing the proteins of the present invention may be used to treat patients suffering from hemophilia caused by deficiency of FVIII.

In practicing the method of treatment of this invention, a therapeutically effective amount of FVIII protein is administered to a mammal having a hemophiliac condition caused by FVIII deficiency. The term "therapeutically effective amount" means the total amount of each active component of the method or composition that is sufficient to show a meaningful patient benefit, i.e. cessation of bleeding.

Administration of the proteins of the present invention can be carried out in a variety of conventional ways. Intravenous administration to the patient is preferred. When administered by intravenous injection, the proteins of the invention will be in the form of pyrogen-free, parenterally acceptable aqueous solutions. A preferred pharmaceutical composition for intravenous injection should contain, in addition to the proteins, an isotonic vehicle such as sodium chloride injection, Ringer's injection, dextrose injection, dextrose and sodium chloride injection, lactated Ringer's injection, or other vehicles as known in the art. The pharmaceutical composition according to the present invention may also contain stabilizers, preservatives, buffers, antioxidants, or other additives known to those of skill in the art.

For cutaneous or subcutaneous injection, the proteins of the present invention will be in the form of pyrogen-free, parenterally acceptable aqueous solutions. The preparation of such parenterally acceptable protein solutions, having due regard to pH, isotonicity, stability, and the like, is within the skill in the art.

As with the pharmaceutical compositions containing the proteins of the present invention, gene therapy delivery systems or vehicles containing nucleotide sequences of the present invention may also be used to treat patients suffering form hemophilia caused by deficiency of FVIII. A therapeutically effective amount of such gene therapy delivery vehicles is administered to a mammal having a hemophiliac condition caused by FVIII deficiency. It will be appreciated that administration of the vehicles of the present invention will be by procedures well established in the pharmaceutical arts, e.g. by direct delivery to the target tissue or site, intranasally, intravenously, intramuscularly, subcutaneously, intradermally and through oral administration, either alone or in combination. It will also be appreciated that formulations suitable for administration of the gene therapy delivery vehicles are known in the art and include aqueous and non-aqueous isotonic sterile injection solutions and aqueous and non-aqueous sterile suspensions.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention as defined in the following claims.

All patents and other publications cited herein are expressly incorporated by reference.

We claim:

1. A procoagulant-active FVIII protein comprising a human FVIII polypeptide that is modified, wherein the modification is a substitution of the Phe309 with Ser.

2. A pharmaceutical composition comprising an effective amount of the protein of claim 1 in admixture with a parenterally acceptable vehicle or excipient.

3. A procoagulant-active FVIII protein comprising a human FVIII polypeptide that is modified, wherein the modification is a substitution of the Arg residue at position 336 with Ile, a substitution of the Arg residue at position 562 with Lys, and a mutation at position 309, and wherein said protein is APC resistant.

4. A pharmaceutical composition comprising an effective amount of the protein of claim 3 in admixture with a parenterally acceptable vehicle or excipient.

5. A pharmaceutical composition comprising an effective amount of the protein of claim 3 in admixture with a parenterally acceptable vehicle or excipient.

6. The protein of claim 3, wherein said protein is capable of increased secretion.

* * * * *

SEQUENCE LISTING

<160> NUMBER OF SEQ ID NOS: 3

<210> SEQ ID NO 1
<211> LENGTH: 162
<212> TYPE: DNA
<213> ORGANISM: Homo sapiens

<400> SEQUENCE: 1
agcttctccc agaattcaag acaccctagc actaggcaaa agcaatttaa tgccaccaca 60
attccagaaa atgacataga gaagactgac ccttggtttg cacacagaac acctatgcct 120
aaaatacaaa atgtctcctc tagtgatttg ttgatgctct tg 162

<210> SEQ ID NO 2
<211> LENGTH: 54
<212> TYPE: PRT
<213> ORGANISM: Homo sapiens

<400> SEQUENCE: 2

Ser Phe Ser Gln Asn Ser Arg His Pro Ser Thr Arg Gln Lys Gln Phe
1 5 10 15

Asn Ala Thr Thr Ile Pro Glu Asn Asp Ile Glu Lys Thr Asp Pro Trp
20 25 30

Phe Ala His Arg Thr Pro Met Pro Lys Ile Gln Asn Val Ser Ser Ser
35 40 45

Asp Leu Leu Met Leu Leu
50

<210> SEQ ID NO 3
<211> LENGTH: 24
<212> TYPE: PRT
<213> ORGANISM: Homo sapiens

<400> SEQUENCE: 3

Ile Thr Phe Leu Thr Ala Gln Thr Leu Leu Met Asp Leu Gly Gln Phe
1 5 10 15

Leu Leu Phe Cys His Ile Ser Ser
20